United States Patent
Nair et al.

(10) Patent No.: US 11,540,909 B2
(45) Date of Patent: Jan. 3, 2023

(54) AZOBENZENE POLYMER NETWORK, AND USES THEREOF FOR BIOFILM REMOVAL AND CONTROL OVER CELL ATTACHMENT

(71) Applicant: THE REGENTS OF THE UNIVERSITY OF COLORADO, Denver, CO (US)

(72) Inventors: Devatha Nair, Denver, CO (US); Robert Mcleod, Boulder, CO (US); Sean Shaheen, Denver, CO (US); Gannon Kehe, Denver, CO (US); Michael Schurr, Aurora, CO (US); Ram Nagaraj, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 453 days.

(21) Appl. No.: 16/639,818

(22) PCT Filed: Aug. 21, 2018

(86) PCT No.: PCT/US2018/047212
§ 371 (c)(1),
(2) Date: Feb. 18, 2020

(87) PCT Pub. No.: WO2019/040425
PCT Pub. Date: Feb. 28, 2019

(65) Prior Publication Data
US 2020/0262993 A1    Aug. 20, 2020

Related U.S. Application Data

(60) Provisional application No. 62/548,095, filed on Aug. 21, 2017, provisional application No. 62/589,439, filed on Nov. 21, 2017, provisional application No. 62/660,745, filed on Apr. 20, 2018.

(51) Int. Cl.

| | |
|---|---|
| B05D 3/02 | (2006.01) |
| B05D 1/40 | (2006.01) |
| C08F 2/46 | (2006.01) |
| C08F 2/50 | (2006.01) |
| C08G 61/04 | (2006.01) |
| A61C 13/087 | (2006.01) |
| C08J 7/04 | (2020.01) |
| A61L 15/24 | (2006.01) |
| A61L 31/10 | (2006.01) |
| B29C 71/02 | (2006.01) |
| C09D 133/14 | (2006.01) |
| C08J 7/043 | (2020.01) |

(52) U.S. Cl.
CPC .......... *A61C 13/087* (2013.01); *A61L 15/24* (2013.01); *A61L 31/10* (2013.01); *C08J 7/043* (2020.01); *C08J 7/0427* (2020.01); *C08J 7/08* (2013.01); *C09D 133/14* (2013.01); *C08J 2333/12* (2013.01); *C08J 2433/14* (2013.01)

(58) Field of Classification Search
CPC ....... C08F 265/06; C08F 222/102; C08J 7/08; C08J 7/043; C08J 7/18; C08J 7/0427; C08J 3/28; C08J 2333/12; C08J 2433/14; C08J 2323/12; C09D 7/65; C09D 151/003; C09D 5/1637; C09D 133/14; C09D 4/06; G03F 7/0002; G03F 7/027; A61L 27/50; A61L 27/34; A61L 15/24; A61L 15/42; A61L 15/46; A61L 31/10; A61L 31/14
USPC ........ 427/385.5, 384, 372.2, 331; 522/6, 71, 522/189, 184, 1; 520/1
See application file for complete search history.

(56) References Cited

U.S. PATENT DOCUMENTS

2005/0135454 A1   6/2005   Wu et al.
2016/0313607 A1   10/2016  White et al.

FOREIGN PATENT DOCUMENTS

| WO | 2009003970 A1 | 1/2009 |
| WO | 2012035302 A1 | 3/2012 |
| WO | 2014162219 A2 | 10/2014 |
| WO | 2018099416 A1 | 6/2018 |

OTHER PUBLICATIONS

Hu et al, Photomodulation of bacterial growth and biofilm formation using carbohydrate-based surfactants, 2016, Chem. Sci., 7, 6628-6634 (Year: 2016).*
Li et al, The light-switching conductance of an anisotropic azobenzene-based polymer close-packedon horizontally aligned carbon nanotubes, 2017, J. Mater. Chem. C, 5, 5068-5075 (Year: 2017).*
International Search Report dated Apr. 24, 2020; International Application No. PCT/US2020/19364; International Filing Date Feb. 21, 2020 (2 pgs).
Kehe, et al., "Optically Responsive, Smart Anti-Bacterial Coatings via the Photofluidization of Azobenzenes" ACS Appl Mater Interfaces, vol. 11, No. 2, Jan. 16, 2019, published online Jan. 4, 2019.

(Continued)

*Primary Examiner* — Jessica Whiteley
(74) *Attorney, Agent, or Firm* — Cantor Colburn LLP

(57) ABSTRACT

Disclosed methods include formulating azobenzene-based polymer networks to induce a modulus change in a highly crosslinked polymer, in vivo, with no external heat requirement and using a benign light as the source of stimuli. A modulus change can be achieved via a coating on the substrate and within the bulk of the substrate via photoexposure. The azobenzene-based polymer network can be formed as a coating or in the bulk of a material from either a glassy composition comprising methyl methacrylate (MMA), poly (methyl methacrylate) (PMMA), and triethylene glycol dimethacrylate (TEGDMA) or a soft material comprising of long-chain difunctional acrylates. The disclosed technology also includes methods of biofilm disruption and removal from the surface of a substrate, and includes methods of inhibiting biofilm growth and cell attachment to a substrate.

12 Claims, 37 Drawing Sheets

(56) References Cited

OTHER PUBLICATIONS

Pubchem (2-Phenyldiazenylphenyl) prop-w-enoate. Dec. 5, 2007, pp. 1-10 [online]; https://pubchem.ncbi.nlm.nih.gov/compound/19862056#section=WIPO-IPC>; p. 2.
Written Opinion dated Apr. 24, 2020; International Application No. PCT/US2020/19364; International Filing Date Feb. 21, 2020 (13 pgs).
Bian, et al., "Light-Triggered Specific Cancer Cell Release from Cyclodextrin/Azobenzene and Aptamer-Modified Substrate" ACS Applied Materials & Interfaces, 2016, vol. 8, 27360-27367.
Hu, et al., "Photomodulation of bacterial growth and biofilm formation using carboydrate-based surfactants" Chemical Science, 2016, vol. 7, (pp. 6628-6634).
International Search Report dated Jan. 4, 2019; International Application No. PCT/US2018/047212; International Filing Date Aug. 21, 2018 (4 pages).
Li et al., "The light-switching conductance of an anisotropic azobenzene-based polymer close-packed on horizontally aligned carbon nanotubes" J. Mater. Chem. C, 2017, vol. 5 (5068-5075).
Written Opinion dated Jan. 4, 2019; International Application No. PCT/US2018/047212; International Filing Date Aug. 21, 2018 (7 pages).

\* cited by examiner

Before Exposure

During Exposure

After Exposure

Before Exposure

During Exposure

After Exposure

Before Exposure

During Exposure

After Exposure

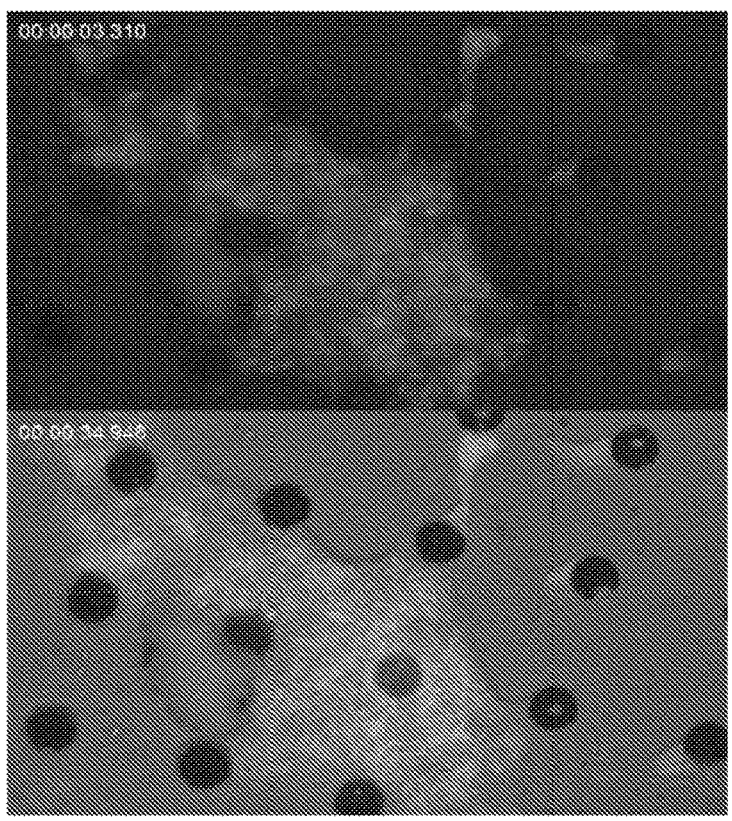
FIG. 22A
FIG. 22B
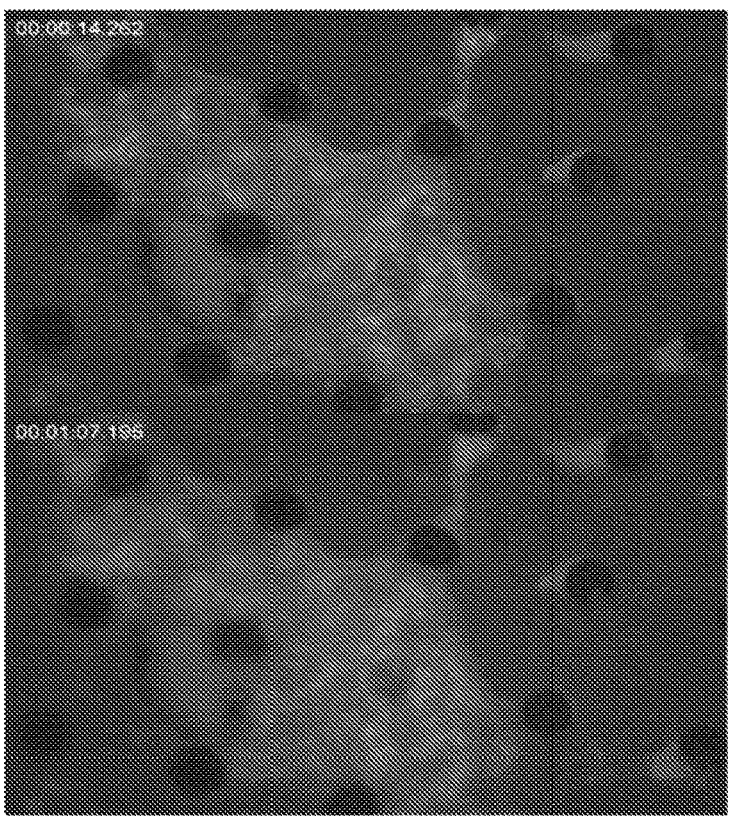
FIG. 22C
FIG. 22D

AZOBENZENE POLYMER NETWORK, AND USES THEREOF FOR BIOFILM REMOVAL AND CONTROL OVER CELL ATTACHMENT

PRIORITY CLAIM

The patent application is a 35 U.S.C. 0.371 National Phase Application of International Patent Application No. PCT/2018/047212, filed Aug. 21, 2018, claiming the benefit of U.S. Provisional Patent Application Ser. No. 62/548,095, filed on Aug. 21, 2017, U.S. Provisional Patent Application Ser. No. 62/589,439, filed Nov. 21, 2017, and U.S. Provisional Patent Application Ser. No. 62/660,745, filed Apr. 20, 2018, which are incorporated herein by reference in their entireties.

TECHNICAL FIELD

This disclosure is directed to azobenzene-based polymer networks on substrate surfaces.

STATEMENT REGARDING FEDERALLY SPONSORED RESEARCH OR DEVELOPMENT

None.

BACKGROUND

When activated by light, heat, and/or a change in pH, photoactive molecules can trigger surface and bulk effects within a system. Light, as a stimulus, is benign in vivo and can be easily controlled and manipulated to instigate a chemical response. When photoactive molecules are introduced into polymer networks, whether passively or through covalent bonding, the photoactive molecules can induce responses within the networks via changes in free volume, both locally and in the bulk material. Uses of photoactive molecules range from photovoltaics and optical nano-writing to surface relief gratings.

SUMMARY

The present disclosure provides methods that include formulating photoactive, azobenzene-based polymer networks to induce a modulus change in a highly crosslinked polymer, in vivo, with no external heat requirement and using benign light as the source of stimuli. In some implementations, the light source may be readily available, ambient light. The azobenzene-based polymer network can be provided as a coating on a substrate or within the bulk of the substrate; the substrate may be a glassy system. A significant modulus change can be achieved by, e.g., photoexposure of the azobenzene-based polymer network. The change in modulus is typically achieved through the addition of heat to the substrate, to drive the azobenzene-based system towards its glass transition temperature ($T_g$). Activating a similar response by utilization of light, rather than heat, results via trans-cis isomerization and/or photofluidization, which can be used in numerous applications in vivo ranging from drug delivery to biofilm removal from numerous devices, systems, and for various other applications, such as inhibiting biofilm growth or even cellular growth.

The disclosed technology also includes methods of biofilm disruption and removal from the surface of a substrate using the ability to engage reversible molecule structures. Specifically, the disclosed technology includes 1) trans-cis isomerization and/or 2) the photofluidization of azobenzenes to enable repeated mechanical removal of biofilm from a substrate "on command." The isomerization and/or photofluidization provides a mechanical disruption to the biofilm that facilitates its removal from the substrate.

The disclosed technology also includes methods of inhibiting biofilm, other film, and cell growth and/or attachment on the surface of the substrate by using the azobenzene-based polymer network.

These and various other features and advantages will be apparent from a reading of the following detailed description.

BRIEF DESCRIPTION OF THE DRAWING

FIGS. 14-29 are images of example biofilm removal methods from example base polymers before and after light exposure and after a gentle wash.

DETAILED DESCRIPTION

Figure 1:
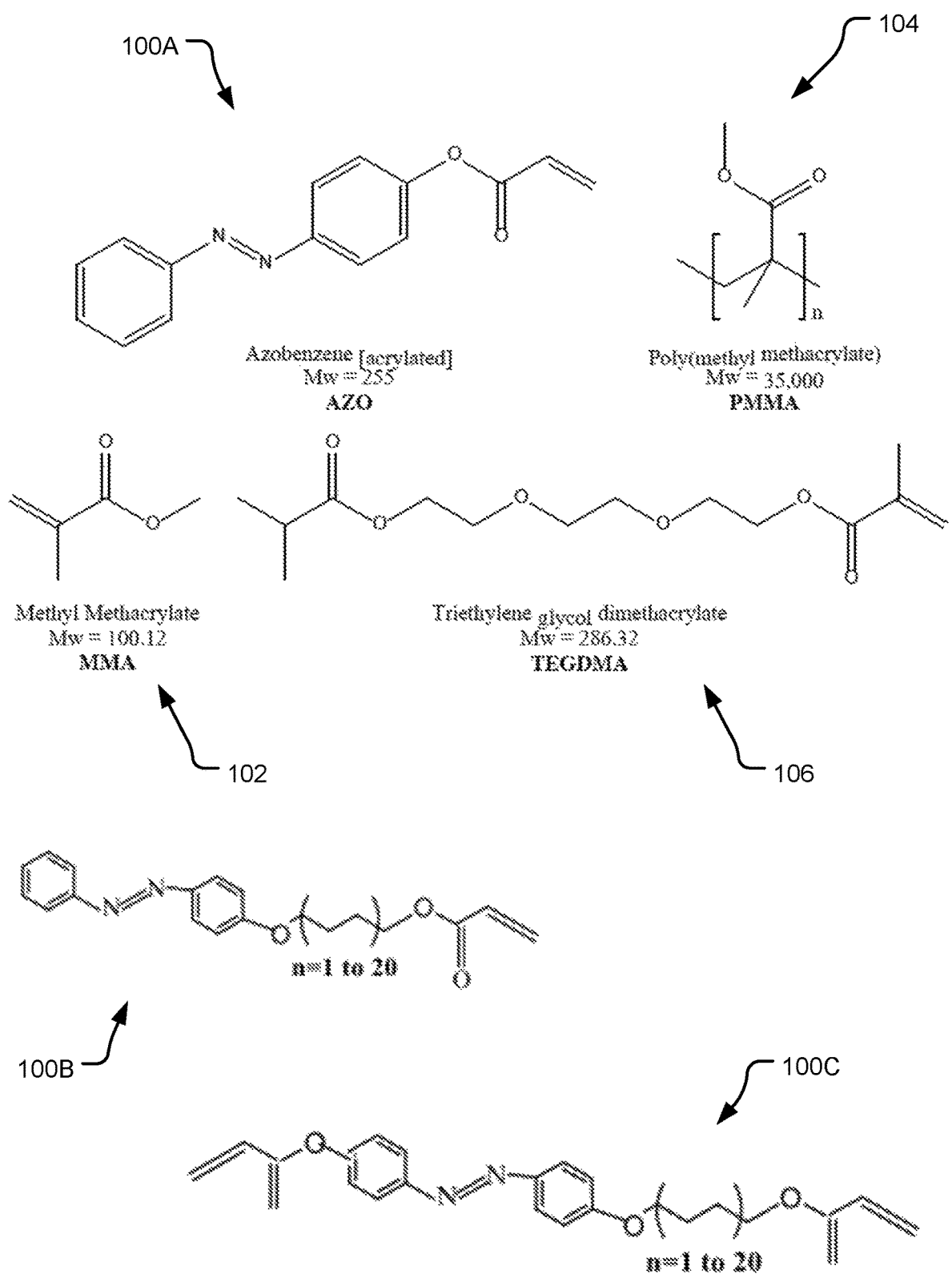
FIG. 1 provides molecular diagrams of example monomers including azobenzene (AZO) and those that can be used in formulating a substrate for an azobenzene (AZO)-based polymer network.

Azobenzene (AZO), a photoactive, photosensitive molecule, has an inherent ability to undergo a trans-cis isomerization under specific wavelengths of light. When an AZO-containing polymer film is irradiated, the isomerization of the covalently tethered AZO molecules within the network induces photo-mechanical stresses, large enough to induce macroscopic deformation of the material. AZO-based polymer networks can change their conformation from trans to cis on exposure to UV light (about 365 nm) and from cis to trans upon exposure to visible light (about 490 nm) or heat. When irradiated with intermediate wavelengths, such as light from a lamp (about 430-480 nm), AZO-based networks undergo rapid and transient, oscillatory trans-cis-trans isomerization, known as a photofluidization effect. The photofluidization effect may induce a change in modulus.

Similar to the trans-cis-trans photoisomerization and/or photofluidization, when an AZO-based network is irradiated with an electric field, the cyclical trans-cis photoisomerization of the AZO groups instigates a reorientation of the molecules, where a main axis of the molecules aligns perpendicular to the electric field. Such reorientation results in the mass migration effect of the AZO molecules as they orient perpendicularly to the electric field. A similar affect can also be achieved by exposing an AZO-based sample to polarized light; the main axis of the molecules aligns perpendicular to the axis of polarization.

This trans-cis-trans photoisomerization and/or photofluidization of AZO-based polymer networks provides a physical dimensional change in the surface of the AZO-based polymer network, and thus disrupts the surface structure and any films (e.g., biofilms) that may be present thereon. Further, the physical dimensional change inhibits the formation or growth of new films (e.g., biofilms, cells).

Disclosed herein are various AZO-based polymer networks, methods of making AZO-based polymer networks, and various applications and uses for the networks, including as coatings on a substrate and within the bulk substrate. The disclosed methods include formulating AZO-based polymer networks to induce a modulus change in a highly crosslinked polymer, in vivo, with no external heat requirement and using benign light as the source of stimuli. A significant modulus change can be achieved, via photoexposure, by having the AZO-network as a coating on a substrate and/or within the bulk of the substrate. Although a change in polymer modulus within a glassy system can be achieved through the application of heat, light, or electric field to the specimen to drive the system towards it glass transition temperature, readily available light (e.g., ambient light) can easily be used in many in vivo applications ranging from drug delivery to biofilm removal to inhibiting future growth.

As indicated above, the AZO-based polymer network is provided either as a surface coating on or within a substrate, the AZO-based polymer network with the substrate being called herein an AZO-based system.

When an AZO-based system is made with a base polymer comprising polymethyl methacrylate (PMMA), the linear PMMA polymer acts as a stabilizer to prevent flow of AZO out from microstructures (e.g., patterned microstructures) formed by the AZO-based polymer network or over which the AZO-based polymer network is coated. This, in effect, triggers a local modulus change within the AZO-PMMA microstructures as the microstructures elongate and contract, or, oscillate. Examples of patterned AZO-PMMA microstructures are cylindrical pillars and pyramids.

The AZO-based systems can be made by combining an AZO-based polymer network with a base polymer formed from, e.g., methyl methacrylate (MMA), poly(methyl methacrylate) (PMMA), and/or triethylene glycol dimethacrylate (TEGDMA). In some implementations, the weight ratio of AZO to the base polymer is 1:4 to 1:15, in other implementations 1:8 to 1:10.

In some implementations, the base polymer is MMA:TEGDMA at a weight ratio of about 1.5:1 to about 4:1, in other implementations about 2:1. In some implementations, particularly ocular devices (e.g., lenses), a 70:30 MMA:TEGDMA weight ratio is suitable.

The MMA may be supplemented with PMMA, e.g., about 20%-25%. That is, PMMA may be present at a weight ratio to the MMA of 4:1 to 3:1 MMA:PMMA.

When the base polymer is MMA:PMMA:TEGDMA, the monomers may be, e.g., at a weight ratio of about 50-60:10-15:25-35; one specific and suitable weight ratio is 56:14:30.

In some implementations, such as when the AZO is incorporated in the bulk of the base polymer, the weight ratio of AZO:(MMA:PMMA):TEGDMA is about 5-15:35-65:20-60. One specific and suitable weight ratio of AZO:(MMA:PMMA):TEGDMA is 11:59:30; this ratio provides a glassy polymer network at room temperature/ambient conditions.

Although acrylated and methacrylated networks such as MMA:PMMA and TEGDMA are described herein for being the base polymer for the system with the AZO, in some implementations, other combinations of monomers that have a glass transition temperature (Tg) can be used. Azobenzenes can be used with any glassy systems or a combination of glassy networks, such as epoxies, as well as Liquid Crystal Networks.

The disclosed technology includes using the AZO-based polymer networks for inhibiting growth of and/or facilitating removal of biofilm from surfaces. Methods disclosed herein include biofilm disruption and removal from a substrate having an AZO-polymer network either on a surface of the substrate (e.g., as a coating) or within the bulk of the substrate. The substrate may be a glass substrate; if the AZO-polymer network is in the bulk of the substrate, the AZO-polymer network may be a glassy network. Depending on the particular composition of the AZO-based polymer network, the AZO-polymer network can be activated by, e.g., light, heat, electric field or current, pH, RF pulse, acoustics, etc. to obtain a change in surface structure and/or modulus, although light is the preferred activator, as it is readily available to the AZO surface. The anchoring force of a biofilm to the surface of a substrate can be disrupted by the AZO-based network physically changing the surface of the substrate structure due to its structure and/or modulus change, resulting in biofilm disruption and removal and inhibiting subsequent biofilm growth thereon.

Alternately to, or in addition to AZO, other molecules may be used in the design of light responsive polymers and thus may be used in the disclosed methods. In addition to AZO, spiropyran, dithienylethene, diazonaphthoquinone, and stillbenes may be suitable polymers to use in the networks and methods of this disclosure. For example, spiropyran has an ability to change shape in response to an external stimulus. These other polymers may be used in addition to or instead of AZO.

The removal of biofilm may be performed on surgical instruments, wound dressings, dental or medical devices and instruments, on dental surfaces (e.g., teeth, composites, fillings), ocular devices (e.g., intraocular lenses, contact lenses), and on other surfaces known for having biofilm thereon. For example, medical procedures such as hemodialysis have high water quality standards that require biofilm removal from the surface of equipment such as piping. As another example, biofilm contamination on contact lenses can be a source of infection for the lens wearer. Incorporating an AZO-based polymer network in or on such device can facilitate the removal of biofilm.

Further, the AZO-based polymer network can be utilized in packaging, plumbing, food production, storage and/or packaging, fermentations processes, water treatment, or other industries where biofilm is commonly present. Pipes, hoses, tanks, valves, pumps, filters, and other equipment may be lined with or have in the bulk substrate the AZO-based polymer networks to facilitate biofilm removal.

In the following description, reference is made to the accompanying drawing that forms a part hereof and in which are shown by way of illustration at least one specific embodiment. The following description provides additional specific embodiments. It is to be understood that other embodiments are contemplated and may be made without departing from the scope or spirit of the present invention. The following detailed description, therefore, is not to be taken in a limiting sense. While the present invention is not so limited, an appreciation of various aspects of the invention will be gained through a discussion of the examples provided below.

As used herein, the singular forms "a," "an," and "the" encompass embodiments having plural referents, unless the content clearly dictates otherwise. As used in this Specification and the appended claims, the term "or" is generally employed in its sense including "and/or" unless the content clearly dictates otherwise.

Spatially related terms, including but not limited to, "lower," "upper," "beneath," "below," "above," "on top," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

FIG. 1 shows chemical structures of several monomers. Molecule 100A is an acylated azobenzene (AZO), specifically, 4-phanolazophenyl acrylate. The AZO 100A commonly has a molecular length of about 10 Angstroms, although longer or shorter molecules may be used. In some implementations, the AZO molecule may be tethered to a longer molecule, to form a molecule of, e.g., 50 Angstroms. Molecule 100B is an AZO with different spacer molecules, and molecule 100C is an AZO with multi-functional azobenzene molecules.

Also in FIG. 1, several monomers are shown that can be used to make a glassy polymer network. Specifically, the monomers include methyl methacrylate (MMA) 102, poly (methyl methacrylate) (PMMA) 104, and triethylene glycol dimethacrylate (TEGDMA) 106. These monomers AZO 100A, AZO 100B, AZO 100C, MMA 102, PMMA 104 and TEGDMA 106 are well known materials and further discussion is not provided herein. The AZO 100A, 100B, 100C is used to form an AZO-based polymer network conducive to removal of biofilm from surfaces, and any or all of MMA 104, PMMA 106 and TEGDMA 108 can be used to form a substrate (e.g., a glass substrate) on which the AZO-based polymer network is provided.

The AZO-based system can formed from AZO-based polymer network mixed with a base polymer, at a weight ratio of AZO to the base polymer of 1:4 to 1:15, in other implementations 1:5 to 1:10. In some implementations, the base polymer is acrylated or methacrylated. As indicated above, examples of suitable base polymers include any of MMA 102, PMMA 104, TEGDMA 106, either alone, in any combination, or in combination with other polymer(s) or monomer(s).

Formation of the AZO-based polymer network and/or the AZO-based system may be facilitated by an initiator or catalyst. For example, light (e.g., visible light, 400-600 nm, and/or UV light, 300-400 nm) or heat can be used to initiate the polymerization. To facilitate the polymerization, a photoinitiator may be added to the mixture; other potential initiators include free radicals, ozone, gamma rays and X-rays.

When the base polymer is MMA and/or PMMA (e.g., the MMA is supplemented with 20%-25% PMMA), the weight ratio of AZO to MMA and/or PMMA is 1:3 to 1:8, in some implementations 1:5 to 1:7; a weight ratio of about 1:6 is one specific and suitable weight ratio.

In some implementations, the base polymer is MMA: TEGDMA (with or without PMMA) at a weight ratio of about 1.5:1 to about 4:1, in other implementations about 2:1. In some implementations, particularly ocular devices (e.g., lenses), a 70:30 MMA:TEGDMA weight ratio is suitable. One specific and suitable weight ratio for many applications is MMA:PMMA:TEGDMA 56:14:30.

In some implementations, such as when the AZO is incorporated in the bulk of the base polymer, the weight ratio of AZO:(MMA:PMMA):TEGDMA is about 5-15:35-65:20-60. One specific and suitable weight ratio of AZO:(MMA: PMMA):TEGDMA is 11:59:30; this ratio provides a glassy polymer network at room temperature/ambient conditions.

Any various adjuvants may be added to the polymeric mixture that forms the AZO-based polymer network or the base polymer; typically, any adjuvants are inactive and do not interfere with the polymerization of the AZO network nor the photofluidization of the AZO network. For example, solvent(s) may be used; examples of suitable solvents include dimethylformamide (DMF), hydroxy ethyl acrylate (HEA).

As indicated above, the AZO-based polymer network is conducive to removal of biofilm from surfaces by its oscillatory trans-cis isomerization (photofluidization effect). The AZO-based polymer network may be present as a coating on the surface of a substrate or may be within the bulk of the substrate or a portion of the bulk of the substrate. The removal of biofilm may be performed on devices such as surgical instruments, wound dressings, dental or medical devices and instruments, dental surfaces (e.g., teeth, dentures, composites, fillings, sealants, etc.), ocular devices (e.g., lenses), food processing equipment and tubulars, and on other surfaces known for having biofilm thereon, which biofilm removal is desired. The thickness of the AZO-based polymer coating on the surface or the amount of AZO in the bulk of the device will differ based on the device; for example, a contact lens will have a thinner coating than a food processing tubular.

The substrate of the device or other apparatus may be metal, plastic (e.g., polymeric), ceramic, rubber, organic (e.g., cotton, cellulosic, wood), or a biologic such as a lens capsular bag and the like, and may include any combinations thereof. The surface of the device may be solid (impermeable) or may be porous; even though solid, solid surfaces may have surface pits and other topography. The device may be opaque, transparent, translucent, or otherwise permeable to light, or even impermeable to light. Although in most implementations the device and its surface are solid and rigid, the device or portions of it may be flexible, conformable, elastic, bendable, etc. The device may be able to withstand sterilization temperatures.

An AZO-based surface coating may be applied directly on to the substrate (e.g., the device), or there may be an intermediate layer, e.g., an adhesion layer, a primer layer, etc., there between. For example, a polymeric base (e.g., MMA:PMMMA:TEGDMA, e.g., a glassy system) may be applied directly on a substrate or device, onto which an AZO-based polymer network coating is applied. As an example, an AZO-based polymer network coating can be applied directly on a tooth or a tooth having a sealant thereon. As another example, an AZO-based polymer coating can be applied directly on a dental composite material or a composite material having a sealant thereon. As another example, an AZO-based system (comprised of an AZO-based polymer network and base substrate) can be applied directly on a sealed or unsealed tooth or composite. An AZO-based polymer network coating may be a preventative for periodontal diseases, thus application on the gingival margins may be desired in some implementations.

Additionally, an AZO-based surface coating may be applied directly on or incorporated into an ocular device, such as a contact lens or an implantable ocular lens. Biofilm formation has been implicated as the causative mechanism in infections with contact lenses, particular biofilms of *Pseudomonas aeruginosa*. An AZO-based polymeric network can be effective at removing biofilms from contact lenses (e.g., silicone acrylate) and also at inhibiting growth of biofilm on the lenses. Because the eye is almost constantly exposed to ambient light, the AZO-coated lens is almost constantly undergoing the trans-cis-trans isomerization and mechanically interrupting the surface of the lens.

The AZO-based polymer network coating may be continuous over the entire surface (e.g., device surface or polymeric substrate surface) or may be present as individual or discrete bands or strips, islands of material, as random islands or blobs of material, etc. The coating can be applied as a gel directly on a biological substrate. The coating may have a constant thickness or may have a varying thickness. As an example, the coating may be continuous over the entire surface, with microstructures (e.g., dots, cylinders, pyramids) present on the continuous coating. As another example, the coating may be individual and discrete microstructures, e.g., evenly, spaced on the surface. As an example, an AZO-based polymer network coating on a contact lens may be nano to micron scale.

The AZO-based polymer network may be incorporated into the bulk of a substrate, or at least into the bulk of the substrate forming the surface on which biofilm accumulates and/or grows. For example, the AZO-based polymer network may be homogenously combined into the substrate, which may be another polymeric network or a composite material, or the AZO-based polymeric network may be heterogeneously present in the substrate, e.g., as orderly bands, rings, layers, islands of material, as random islands or blobs of materials, or randomly and irregularly throughout the substrate or proximate the surface of the substrate. In some implementations, the AZO-based polymeric network may be present as a surface layer in the bulk of and integral with the substrate.

The following non-limiting examples were prepared, showing various methods of forming AZO-based polymer networks and applying those networks to surfaces and within substrates for biofilm removal.

A first glassy polymer network was made with MMA:PMMA:TEGDMA in a weight ratio of 56:14:30 (20% of MMA supplemented with PMMA); this polymer network was used as a base polymer substrate (BPS). The composition of MMA:PMMA:TEGDMA monomers illustrates the photoinduced softening of a rigid polymer network via the presence of AZO moieties. In one formulation, a composition was polymerized via UV free-radical initiated polymerization to a conversion of ~80% (observed via FTIR) to form a very glassy base polymer substrate (BPS). Substrates were prepared from the BPS using photoinitiator "Irgacure 819" (IR 819) available from Ciba Special Chemicals. AZO surface coatings were covalently tethered to the BPS with thermal initiator-AIBN. AZO in the bulk was prepared using thermal initiator-AIBN. The solvent for a surface coating composition was N,N-Dimethylformamide. Acrylation tethered the AZO into the backbone of crosslinked polymer.

Figure 2:
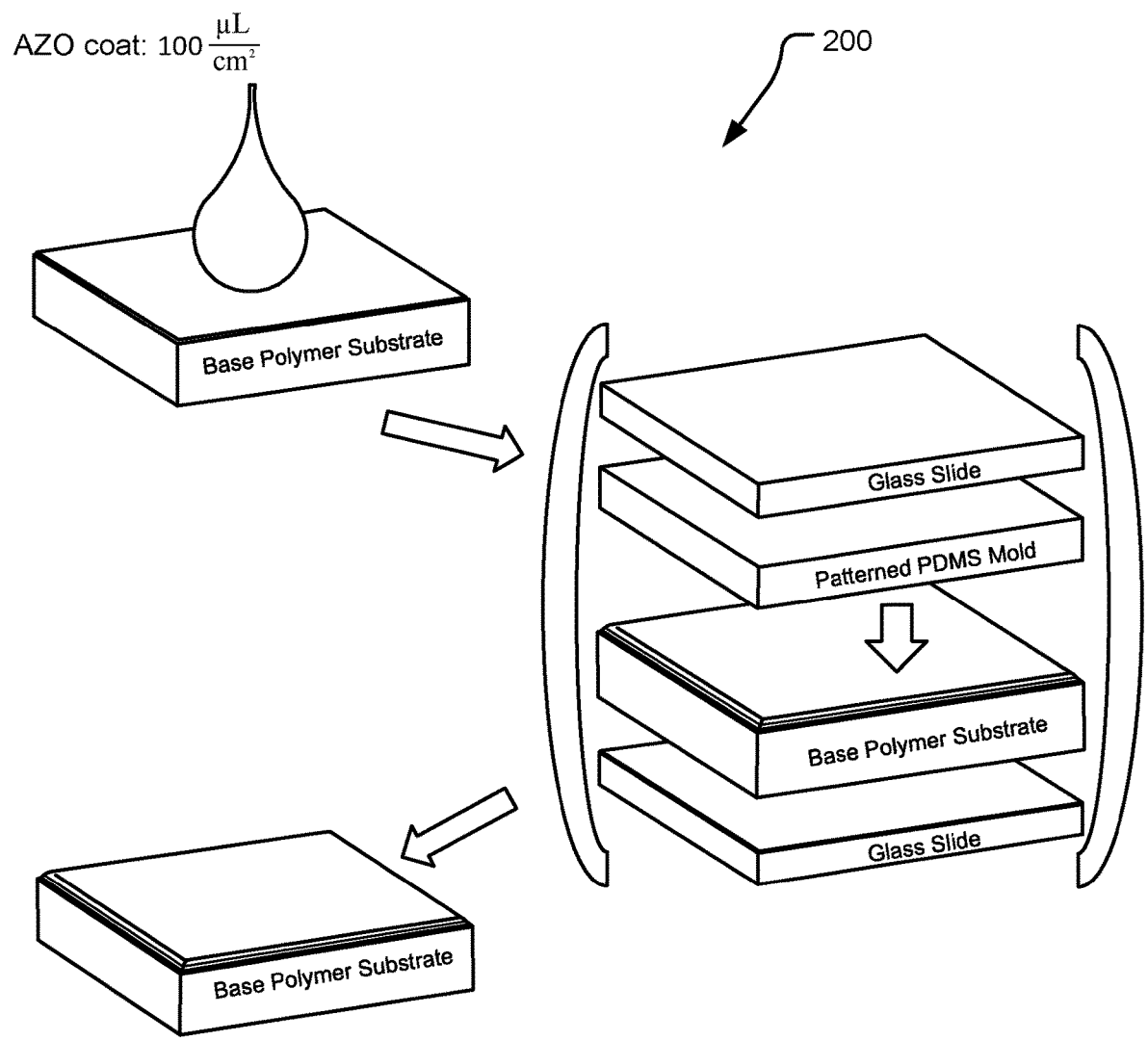
FIG. 2 is a schematic diagram of steps for an example method of making an AZO-based polymer network on a base substrate.

FIG. 2 is a schematic, semi-step-wise diagram of an example method 200 for making an AZO-based system, composed of an AZO-based polymer network and a base substrate (BPS). The method includes the following example protocols, the first of which is generally shown in FIG. 2:

Example Protocol for Base Polymer Substrate (BPS)

1. Mix (MMA:PMMA):TEGDMA in weight fractions 70:30 and stir over heat until a homogeneous mixture is formed.
2. Allow mixture to cool and then add 0.1 weight % photoinitiator (IR 819).
3. Insert Base Polymer monomer solution between two glass slides with a 0.75 mm spacer and clamp together.
   a. Obtain IR spectrum (initial).
4. Photocure to 80% conversion using 365 nm light at an intensity of 200 mW/cm$^2$.
   b. Obtain cured IR spectrum (final).
5. Ensure conversion of base polymer has reached at least 90%.
6. Extraction
   a. Swell the cured based polymer in acetonitrile for 48 hours.
   b. Gently pour off acetonitrile.
   c. Cover vial with parafilm with poked holes and leave in fume hood for 24 hours at room temperature.
   d. Place sample in vacuum oven at 60° C. for 24 hours.
   e. If observe any cracks in the film, discard the sample, otherwise proceed to next step.
   f. Measure the acrylate conversion on extracted sample.
   g. Run the Dynamic Mechanical Analysis (DMA) on the extracted sample and compare it with that of the Tg before extraction.

Example Protocol for Surface Coatings (Control Samples) (SCF)

1. Mix 0.5 weight % Rhodamine B Acrylate and 1 weight % AIBN in dimethylformamide (DMF).
2. Deposit 100 µL/cm$^2$ of mixture on polymer substrate surface on the opposite side of direct UV radiation from polymerization (portion of polymer with lowest conversion).
3. Allow coating solvent to evaporate at room temperature for 1 hour (without mold).
4. Insert polydimethylsiloxane (PDMS) mold and coated polymer substrate between two glass slides.

5. Obtain IR spectrum for conversion calculations (initial).
6. Thermal cure in oven at 80° C. for 4 hours (vacuum "on" to eliminate solvent).
7. Obtain cured IR spectrum or conversion calculations (final).
8. Wash cured coated polymer in water for 1 hour.
9. Dry sample in hood for 24 hours.
10. Dry sample in oven at 60° C. for 24 hours (vacuum on).

Example Protocol for AZO Coating (Biofilm Testing and Confocal Imaging) (AZO-SC)
1. Mix 50 mg/mL of acrylated AZO with 0.5 weight % Rhodamine B Acrylate and 1 weight % AIBN in DMF; mix until homogenous and avoid heat.
2. Deposit 100 µL/cm² of mixture on polymer substrate surface on the opposite side of direct UV radiation from polymerization (portion of polymer with lowest conversion).
3. Allow coating solvent to evaporate at room temperature for 1 hour (without mold).
4. Insert PDMS mold and coated polymer substrate between two glass slides.
5. Obtain IR spectrum for conversion calculations (initial).
6. Thermal cure in oven at 80° C. for 4 hours.
7. Obtain cured IR spectrum for conversion calculations (final).
8. Wash cured coated polymer in water for 1 hour.
9. Dry sample in hood for 24 hours.
10. Dry sample in oven at 60° C. for 24 hours (vacuum "on").

Example Protocol for AZO in the Bulk Polymer (AZO+BPF).
1. Mix AZO:(MMA:PMMA):TEGDMA in weight fractions 11:59:30 and stir over heat until a homogeneous mixture is formed.
   a. If sample is being used for confocal microscopy, add 0.1 weight % Rhodamine B (acrylated) to AZO:(MMA:PMMA):TEGDMA mixture.
2. Allow mixture to cool and then add 1.0 weight % thermal initiator (AIBN).
3. Sandwich AZO:(MMA:PMMA):TEGDMA monomer solution in a 0.75 mm spacer between two glass with a 2.1 µm thick hexagonal patterned PDMS mold and clamp together.
   a. Obtain IR spectrum (initial).
   b. If the specimen is being used for DMA, then the PDMS mold is not necessary and the monomer solution can simply be cured between two glass slides.
4. Thermal cure in oven at 80° C. for 12 hours to achieve at least 90% conversion.
   a. Obtain cured IR spectrum (final).
5. Ensure conversion of base polymer has reached at least 90%.

6. Remove sample from curing apparatus and fix the sample to a glass slide for confocal imaging or take dimensional measurements for DMA.
7. If Extraction is required, follow "step 6: Extraction" under Protocol for Base Polymer Substrate.

Conversion Calculations:
Base Polymers:(MMA:PMMA):TEGDMA (70:30) photocard under UV (365 nm)

| Time (min)     | 0      | 15    | 30    | 45    |
|----------------|--------|-------|-------|-------|
| Peak Area (IR) | 17.253 | 4.13  | 3.729 | 3.476 |
| Conversion (%) | 0      | 76.062| 78.386| 79.853|

AZO Surface Coating: thermal cured at 80° C.

| Time (hours)   | t = 0 (initial) | t = 12 hrs (final) |
|----------------|-----------------|--------------------|
| Peak Area (IR) | 2.988           | 0.145              |
| Conversion (%) | 0               | 95.147             |

AZO in Bulk (AZO+Base Polymer): Thermal cured at 80° C.

| Time (hours)   | t = 0 (initial) | t = 12 hrs (final) |
|----------------|-----------------|--------------------|
| Peak Area (IR) | 7.777           | 0.547              |
| Conversion (%) | 0               | 92.966             |

Example Protocol for Soft Lithography
1. Silicon master chip fabricated using photolithography methods and AZ 4210 photoresist to create and array of 2.1 µm thick hexagons.
2. Hexagonal pattern transferred to PDMS mold using soft lithography methods
   a. Mix "Sylgard 184" base and curing agent in a 7.5:1 weight ratio and mix for 3-5 min, until completely homogeneous mixture is formed.
      1) If a more rigid PDMS stamp is required increase the curing agent content.
   b. Place the mixture in a desiccator and turn on vacuum.
   c. Allow the mixture to remain under vacuum until all the bubbles generated from mixing are removed.
   d. Ensure the surface of the master chip is free of any impurities (rinse with IPA and let dry in hood).
   e. Place a spacer with the desired size of the PDMS mold cut out of the center on top of the master chip.
   f. Pour the Sylgard mixture into the cut out spacer on top of the master chip.
   g. Place the master chip/spacer/Sylgard mix in the oven at 80° C. for 3 hours with vacuum on to ensure no bubbles are retained in the PDMS mold.
   h. Remove sample from the oven and cut away the spacer and excess PDMS so that only patterned surface remain.

Example Protocol for Confocal Microscopy Imaging (Video)

| Test Type | Light Exposure (maintaining a 1-2° C.) temperature Rise | Hot Air Test | Cool Air Test | Simultaneous Hot Air and Light Exposure Test |
|-----------|---------------------------------------------------------|--------------|---------------|----------------------------------------------|
| Video Started (sec)   | t = 0 sec  | t = 0 sec  | t = 0 sec  | t = 0 sec  |
| Stimuli Initiated (sec) | t = 10 sec | t = 10 sec | t = 10 sec | t = 10 sec |
| Stimuli removed       | t = 1 min  | When pattern disappears | When pattern disappears | When pattern disappears |

| Test Type | Light Exposure (maintaining a 1-2° C.) temperature Rise | Hot Air Test | Cool Air Test | Simultaneous Hot Air and Light Exposure Test |
|---|---|---|---|---|
| Video Terminated (sec) | t = 2 min | When pattern reappears or image becomes unchanged for more than 1 min | When pattern reappears or image becomes unchanged for more than 1 min | When pattern reappears or image becomes unchanged for more than 1 min |

1. Light source for imaging is the 3M Elipar™ DeepCure-S LED Curing Light.
   a. Wavelength=430-480 nm with a Maximum Intensity 1,470 mW/cm².
   b. Light source held at a constant 2 cm distance from sample to generate an irradiance intensity of 700 mW/cm².
2. Images, videos, and z-stacked images were obtained using a Nikon TI Eclipse Confocal Microscope.
3. Fluorescent used: Acryloxyethylthiocarbamayol Rhodamine B (excitation wavelength=570 nm).
   a. Obtained from PolySciences Inc.
   b. Fluorescent content=0.5 weight % of composition.
4. Imaging Laser: TRITClaser with a wavelength of 561 nm.
5. 20× Magnification must remain constant (imaging may be cropped using NIH software).

Figure 3:
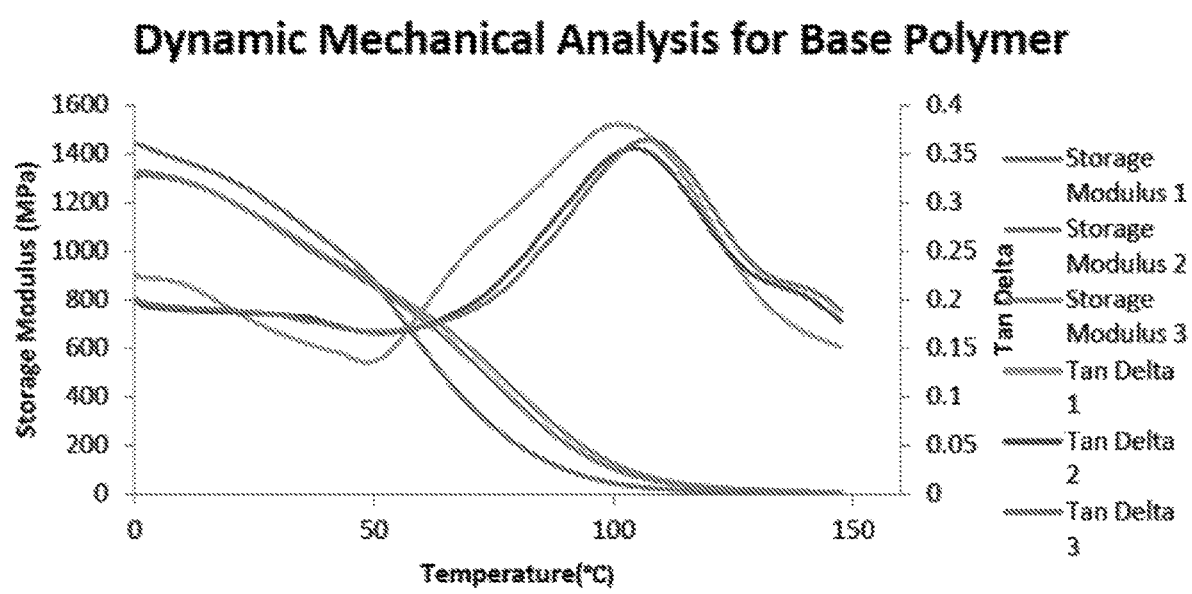
FIG. 3 is a graphical representation of dynamic mechanical analysis of an example base polymer.

FIG. 3 is a graph of dynamic mechanical analysis (DMA) for an (MMA:PMMA):TEGDMA (70:30) base polymer prepared as per above, showing temperature vs. storage modulus (Mpa). DMA on the film confirmed a glass transition temperature ($T_g$) of 105° C.

Figure 4:
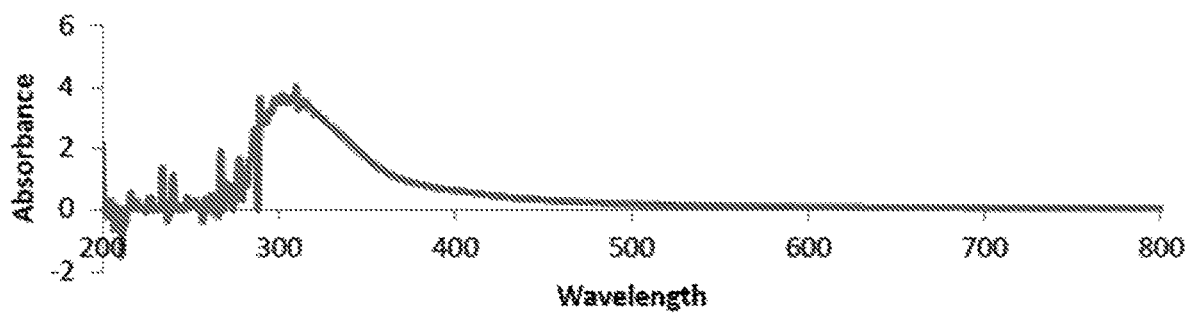
FIG. 4 is a graphical representation of UV-VIS spectroscopy for an example base polymer substrate (pre-coated).

FIG. 4 is a graph of a UV-VIS spectroscopy showing wavelength vs. absorbance of the prepared example (MMA:PMMA):TEGDMA (70:30) base polymer, prior to any coating.

Figure 5:
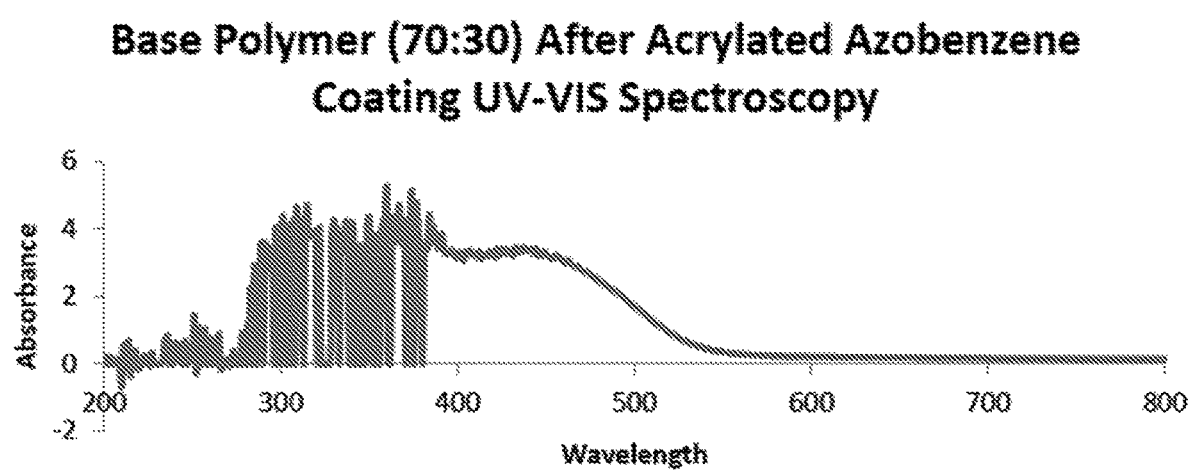
FIG. 5 is a graphical representation of UV-VIS spectroscopy for an example base polymer substrate having an acrylated AZO coating.
Figure 6A:
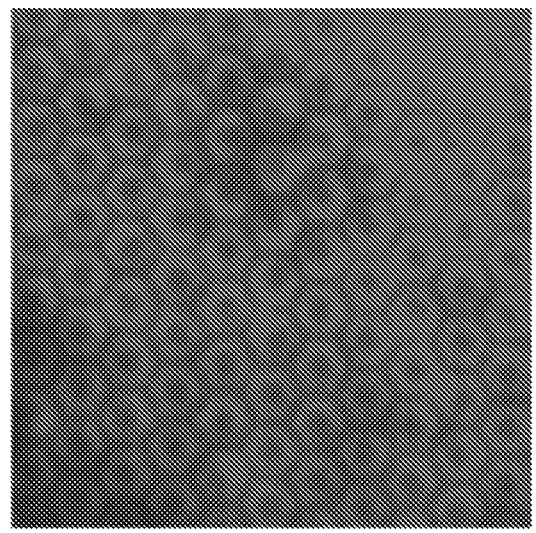
FIGS. 6A, 6B and 6C are photomicrograph images of an example base polymer before, during, and after exposure to visible light.
Figure 6B:
Figure 6C:
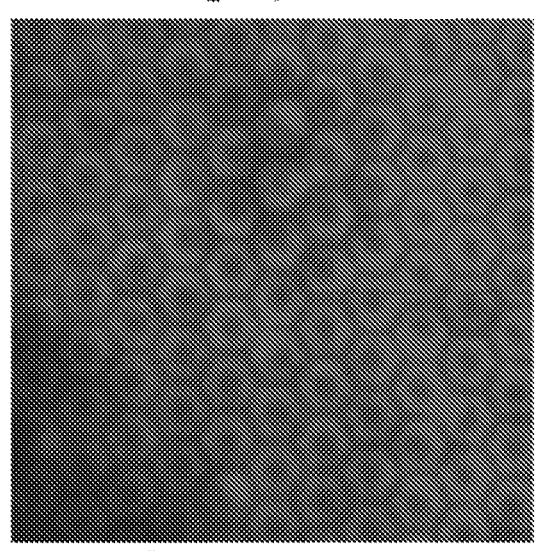

FIG. 5 is a graph of a UV-VIS spectroscopy measuring wavelength vs. absorbance of the example base polymer after coating with acrylated AZO.

A surface coating composition (SCF) containing 50 mg/ml of acrylated AZO and a thermal initiator, AIBN, in DMF was developed on the base polymer substrate (BPS) and thermally cured. A glassy surface coating containing acrylated AZO tethered to the surface of the BPS was obtained.

In sequence with coating the BPS, UV-VIS spectroscopy was run on the uncoated BPS and the coated BPS; the results are illustrated in FIG. 4 and FIG. 5, respectively. A fairly substantial shift in absorbance was observed; the absorption spectrum shifts from 270-500 nm for the uncoated BPS to 270-550 nm for the AZO-coated BPS. It was observed that the acrylated AZO surface coating (AZO-SC) attributes to an increase in the rate of absorption and magnitude at specific wavelengths.

FIGS. 6A, 6B, 6C and FIGS. 7A and 7B are photomicrograph images of an example base polymer before, during, and after exposure to visible light. For FIGS. 6A, 6B, 6C, AZO was dropcasted on a base polymer and exposed to light while maintaining less than a 1° C. temperature rise. It was observed that the patterned AZO-SC (FIG. 6A) underwent a change in height as observed by the darkening of the image (FIG. 6B) while exposing the sample to visible light from a 3M Elipar™ DeepCure-S LED Curing Light with a wavelength of 430-480 nm and intensity of 700 mW/cm². This indicates a change in the focal plane of the confocal microscope. Upon removal of the light (FIG. 6C) the patterned AZO-SC returned to its initial state.

Figure 7A:
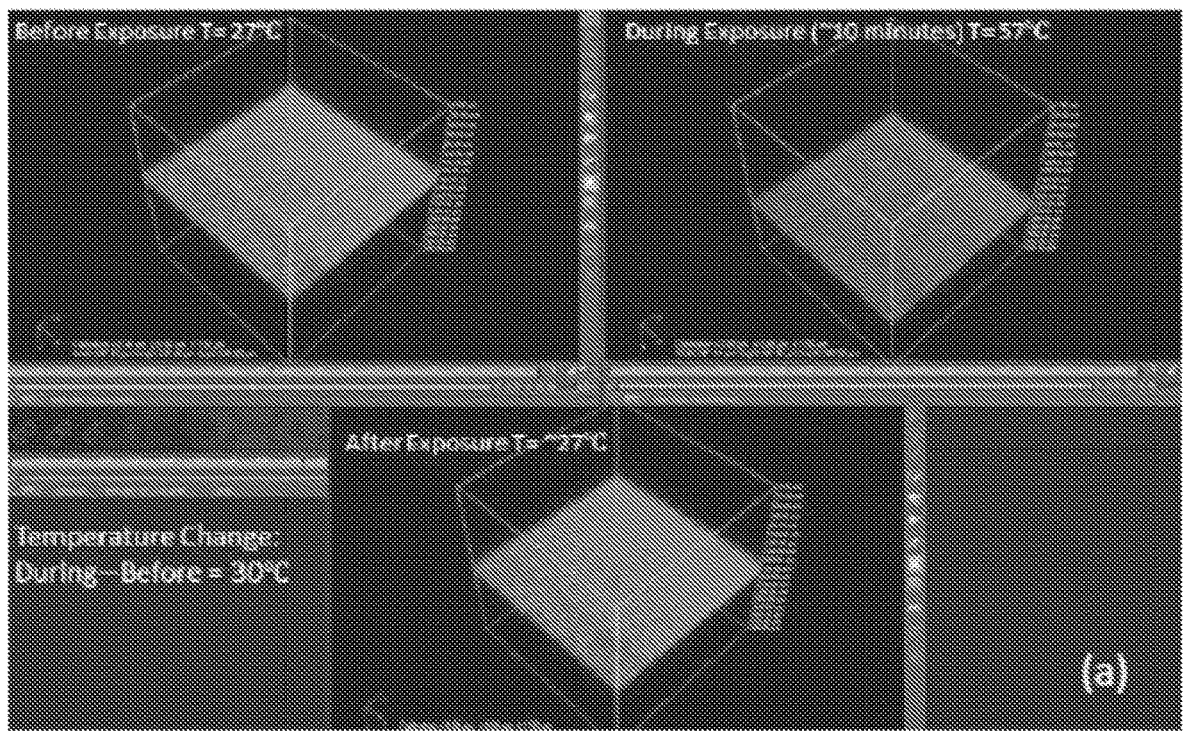
FIGS. 7A and 7B each have images of an example base polymer before, during, and after exposure to visible light.
Figure 7B:
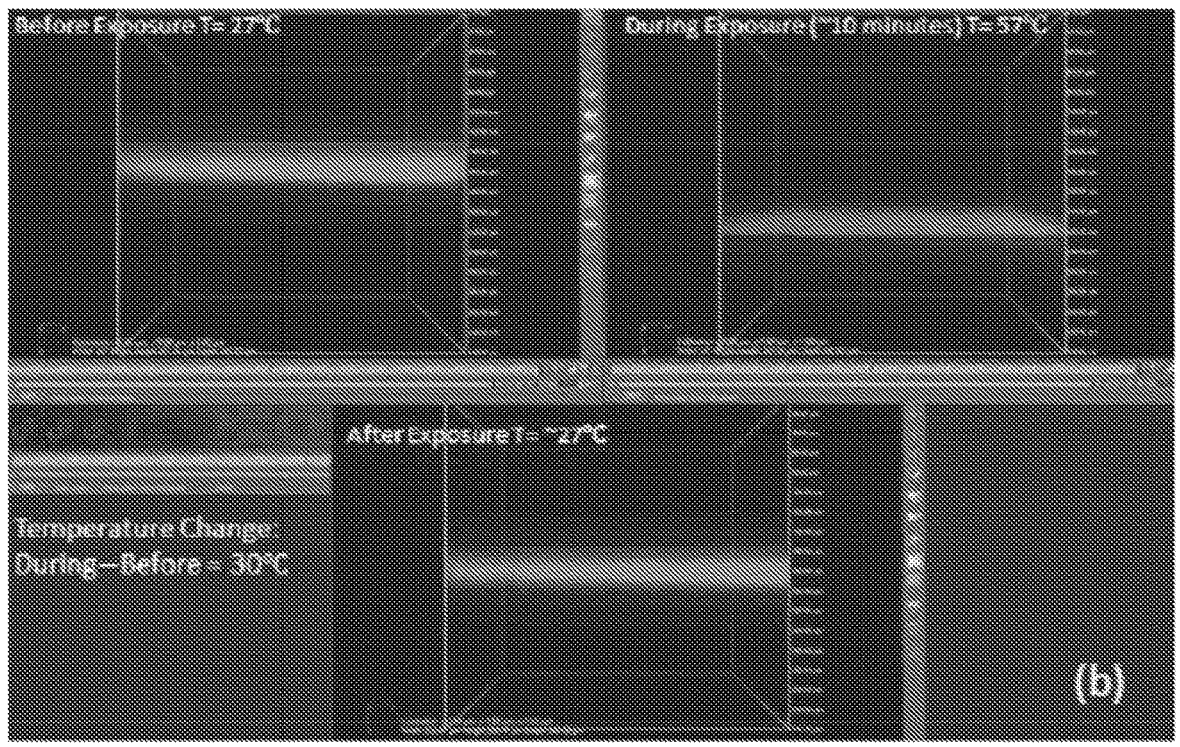

Referring to FIGS. 7A and 7B, the pattern disappearance was studied further by obtaining z-stacked images of the AZO-SC over a constant imaging volume depending on the sample size (~280 µm). AZO was dropcasted on a base polymer, with light exposure for the entirety of "exposed Z-stack image" (~10 minutes), ΔT=30° C. A reduction in depth of the AZO-SC by ~70 µm was observed. It should also be noted that the temperature of the system increased by 30° C.

Figure 8A:
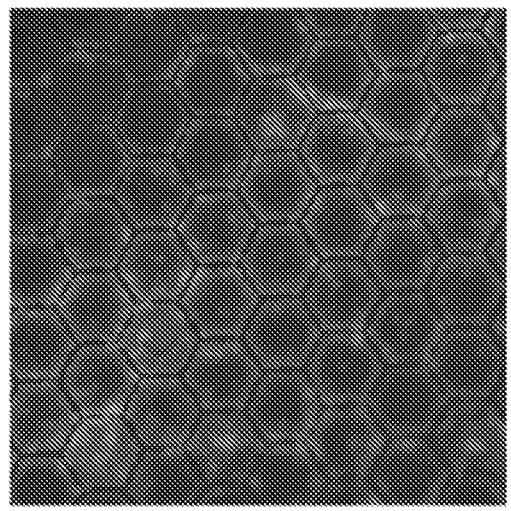
FIGS. 8A, 8B and 8C are photomicrograph images of an example base polymer before, during, and after exposure to visible light.
Figure 8B:
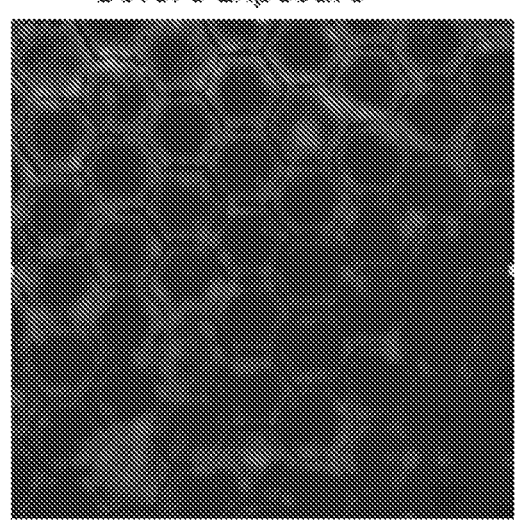
Figure 8C:
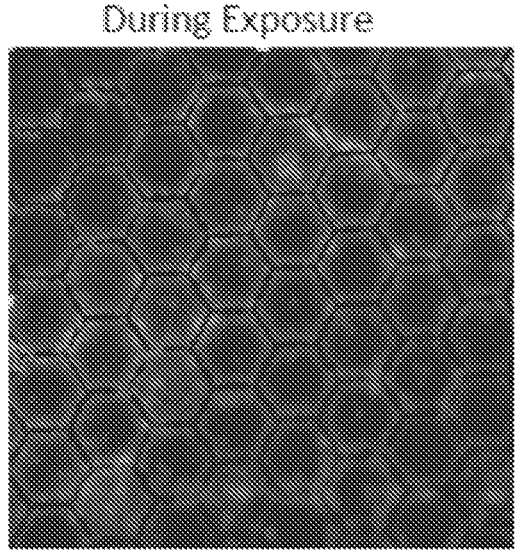

FIGS. 8A, 8B, 8C are photomicrograph images of another example base polymer before, during, and after exposure to visible light. In order to distinguish whether this depth change was a temperature effect or a product of the AZO in the SCF; further imaging was conducted while constricting the temperature rise of the system to no more than 2° C. Samples were developed for confocal imaging by adding Rhodamine B to the SCF and patterning the AZO-SC in an array of hexagons on the surface of the BPS. An identical confocal test done on a control sample containing only Rhodamine B and no AZO resulted in no change in surface coating depth when the control sample was irradiated with the same light source. The Rhodamine control was dropcasted, with light exposure while maintaining less than a 1° C. temperature rise. The results showed that the depth change of the surface coating was a product of the AZO in the SCF.

To determine whether the presence of AZO within the bulk of a glassy network would demonstrate a similar photosoftening effect, a BPS composition that included AZO in the bulk was developed. Monomers AZO:(MMA:PMMA):TEGDMA in weight a ratio of 11:59:30 were thermally cured with AIGN at 1 weight % and Rhodamine B at 0.1 weight % (referred to as AZO+BPF) (20% of original MMA content replaced with AZO). The monomer mixture was sandwiched between two glass slides and thermal cured for 12 hours to 93% conversion.

Figure 9:
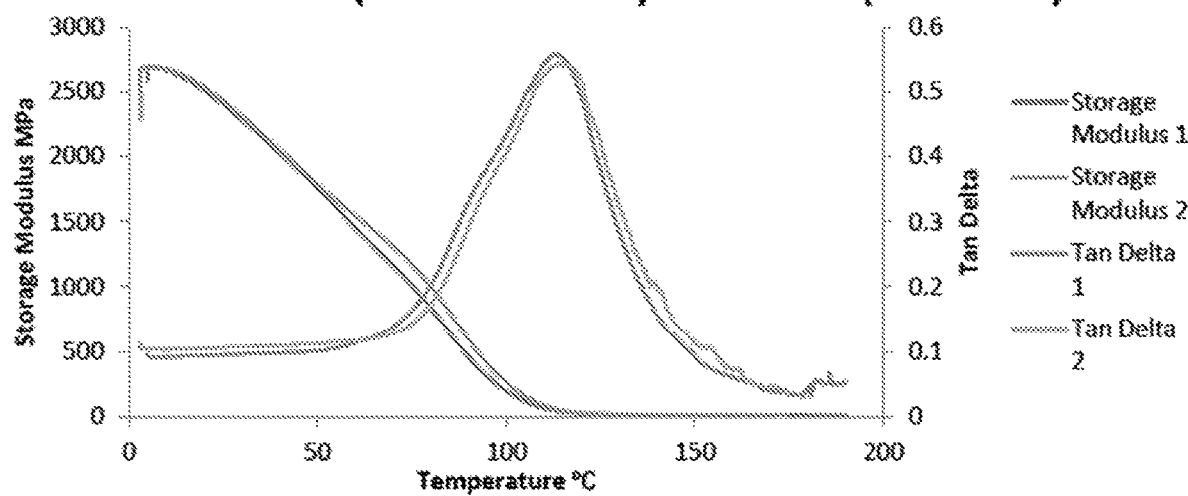
FIG. 9 is a graphical representation of a dynamic mechanical analysis of AZO in an example bulk substrate.

FIG. 9 is a graph of dynamic mechanical analysis for AZO in an example bulk substrate formed from a composition of AZO:(MMA:PMMA):TEGDMA (11:59:30). The graph shows the temperature vs. storage modulus (Mpa). After curing, DMA analysis confirmed a glassy polymer at 22° C. and a $T_g$ of 113° C.

Figure 10A:
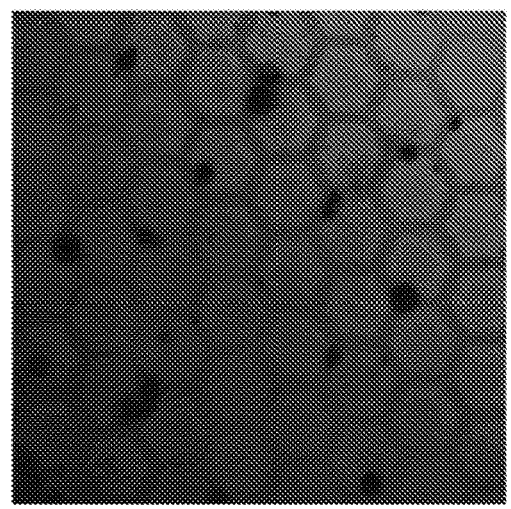
FIGS. 10A, 10B and 10C are photomicrograph images of an example base polymer before, during, and after exposure to visible light.
Figure 10B:
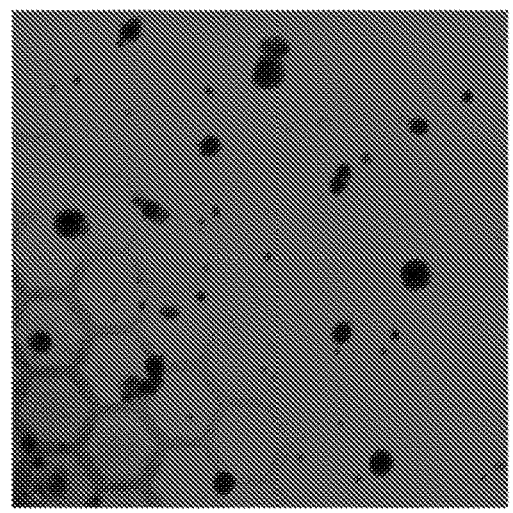
Figure 10C:
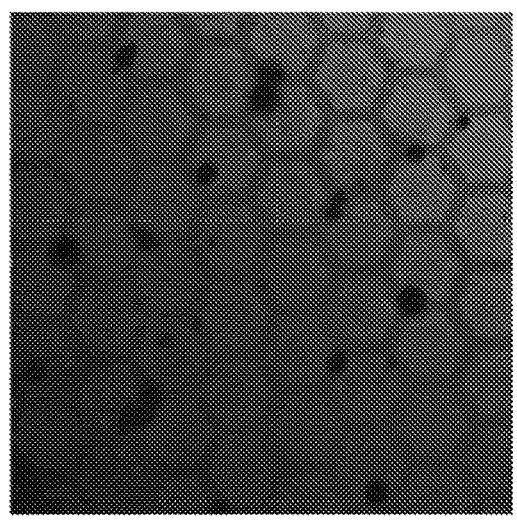

FIGS. 10A, 10B, 10C are photomicrograph images of another example base polymer before, during, and after exposure to visible light. The hexagonal surface patterned sample of AZO+BPF was imaged under a confocal microscope to observe the effect AZO has on the bulk polymer, while maintaining less than a 1° C. temperature rise. Similar to the images obtained for the AZO-SC (FIGS. 8A, 8B, 8C), a disappearance of the patterned surface and a corresponding depth charge during light exposure with a nominal temperature rise for the AZO+BPF was generated.

Figure 11A:
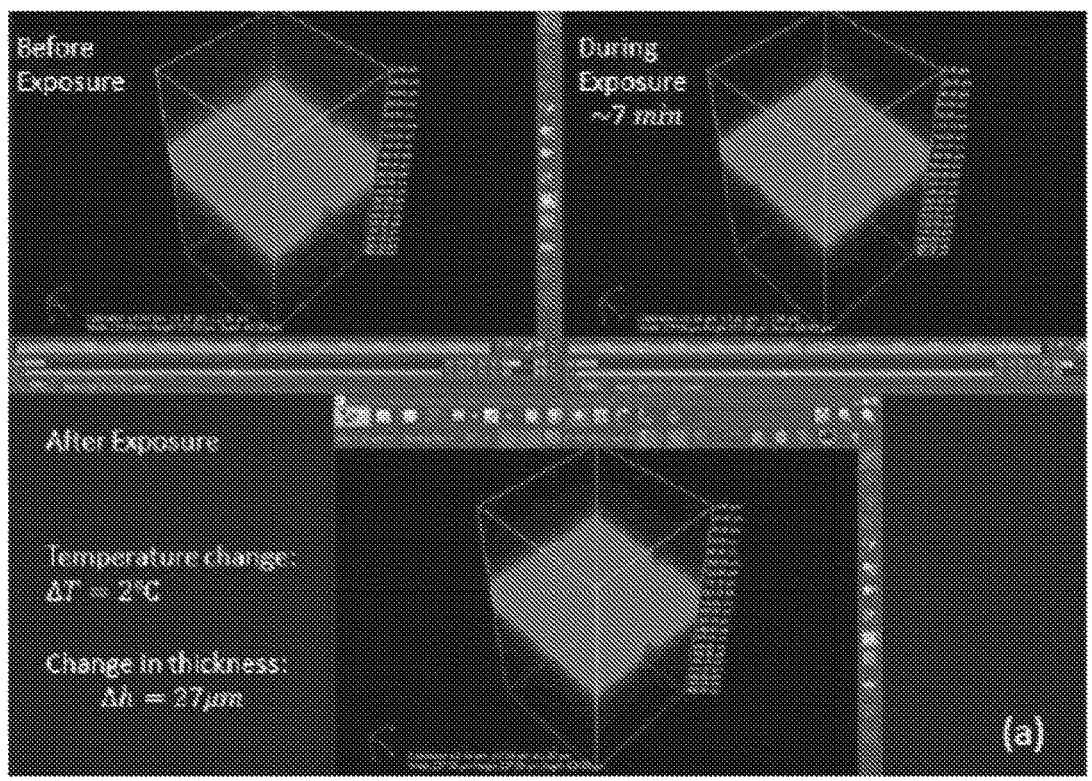
FIGS. 11A and 11B each have images of an example base polymer before, during, and after exposure to visible light.
Figure 11B:
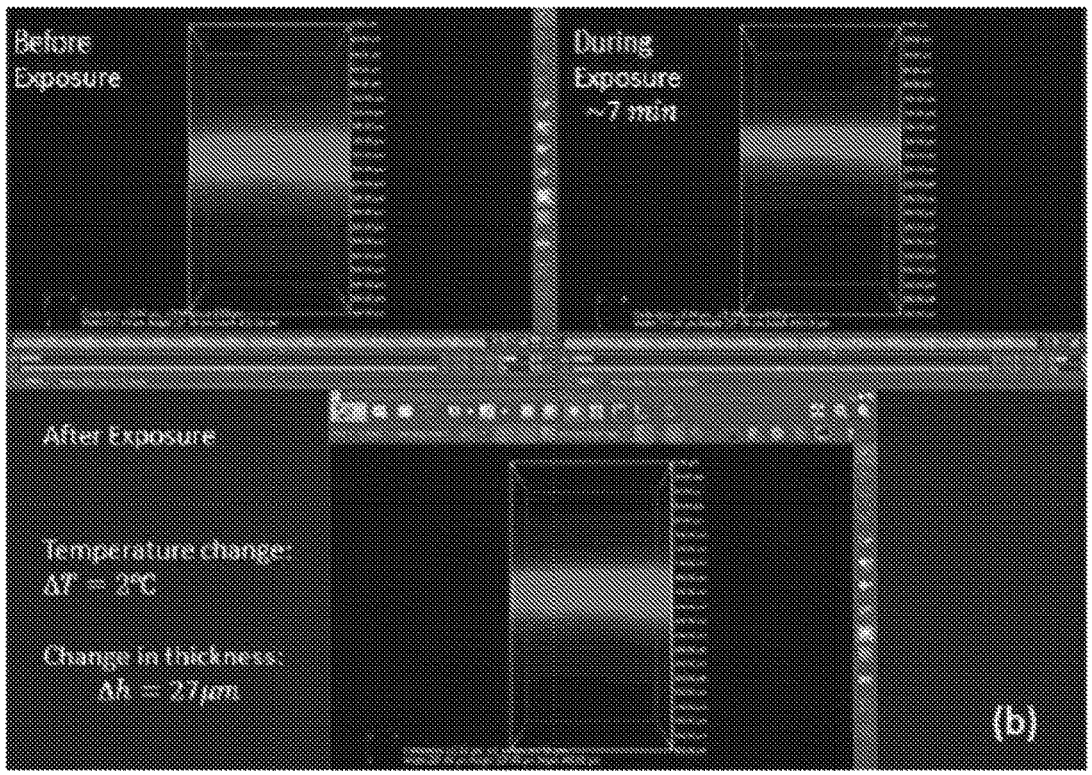

FIGS. 11A and 11B are photomicrograph images of an example base polymer before, during, and after exposure to visible light. When obtaining z-stacked images before, during, and after light exposure it was observed that the bulk polymer as a whole was shrinking. The height change of the AZO coating layers and the AZO+BPS before/after exposure and during exposure to visible light was calculated to be about 27 µm.

Figure 12A:
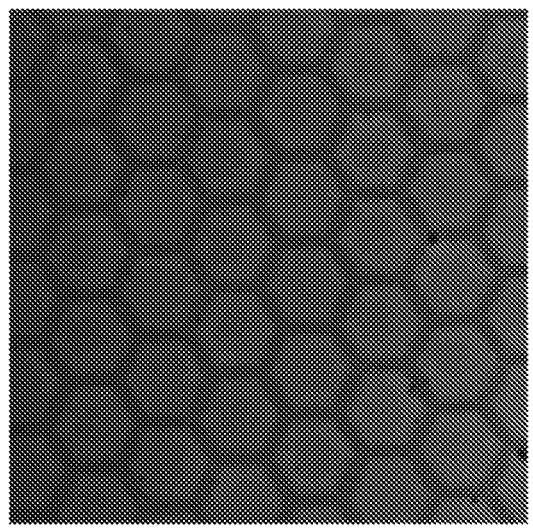
FIGS. 12A, 12B and 12C are photomicrograph images of an example base polymer before, during, and after exposure to visible light.
Figure 12B:
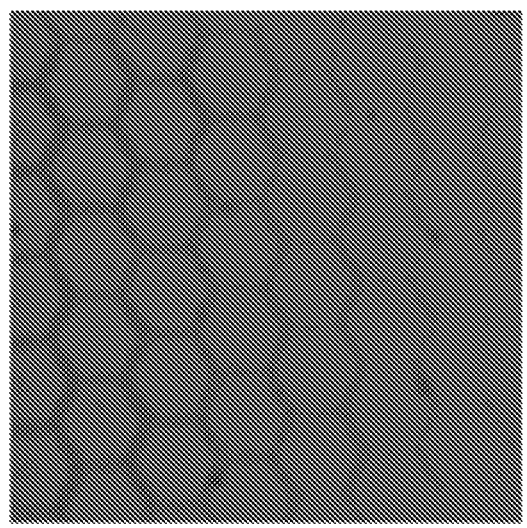
Figure 12C:
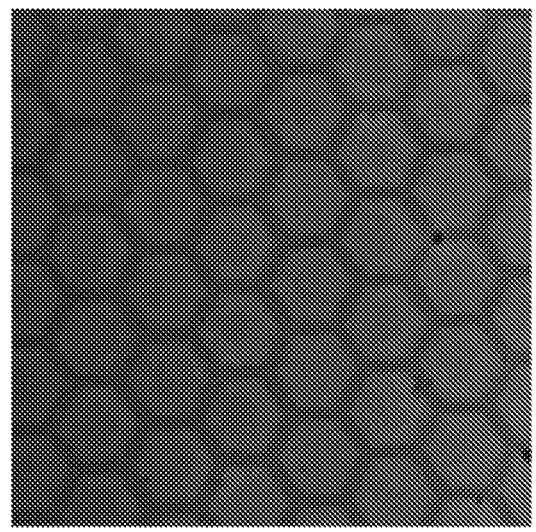

FIGS. 12A, 12B, 12C are photomicrograph images of an example base polymer before, during, and after exposure to visible light. FIGS. 12A, 12B, 12C show a control sample that contained no AZO with a change in surface depth in the control system.

Figure 13A:
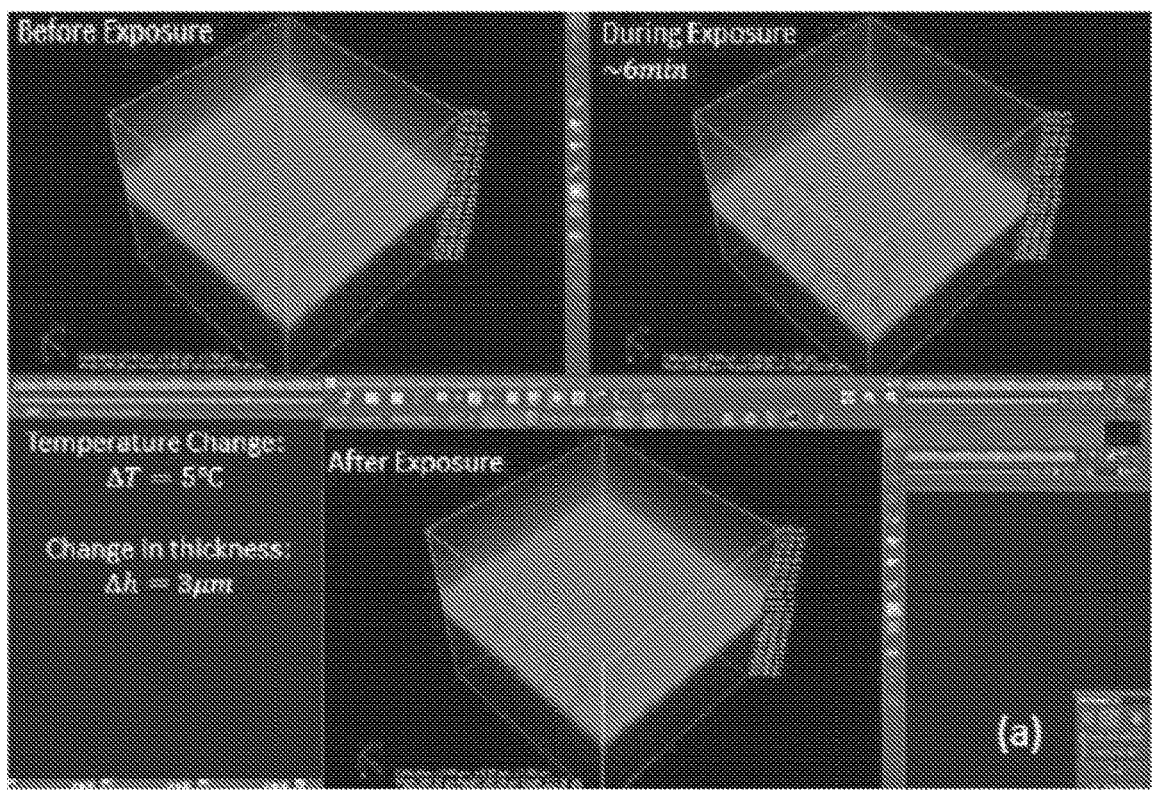
FIGS. 13A and 13B each have images of an example base polymer before, during, and after exposure to visible light.
Figure 13B:
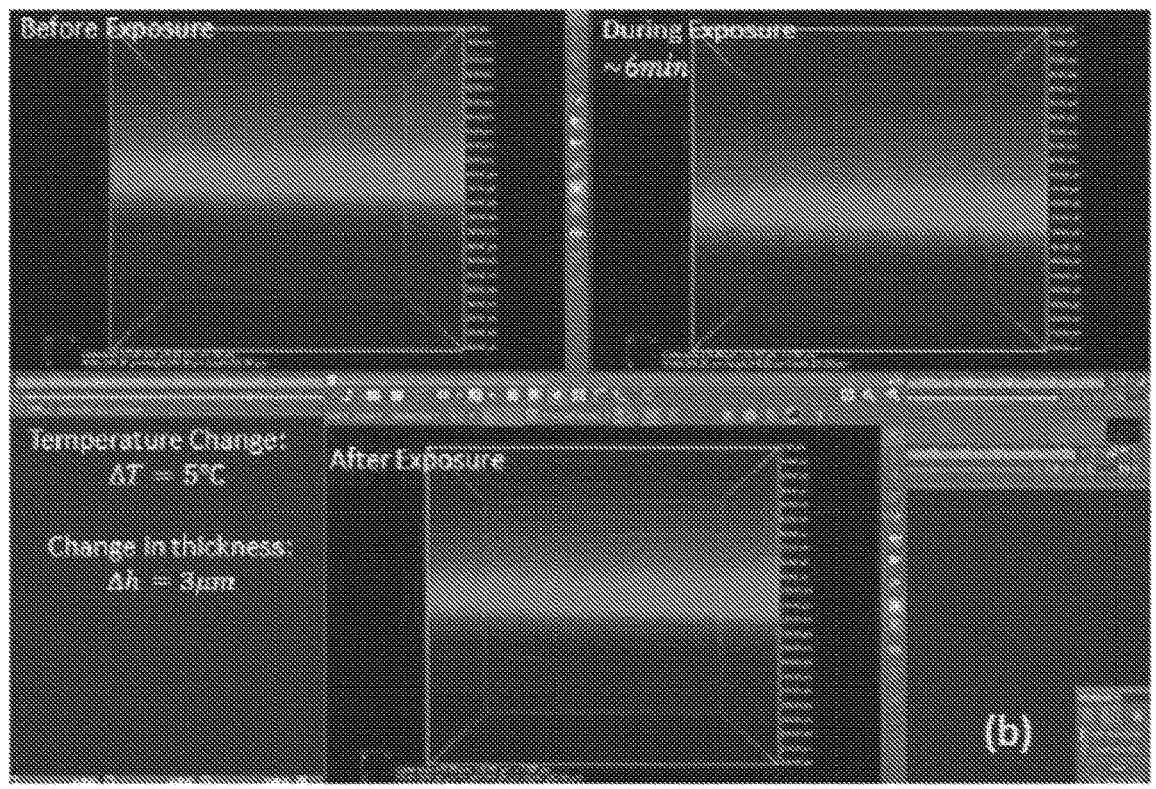

FIGS. 13A and 13B are z-stacked images of an example base polymer before, during, and after exposure to visible light. The z-stacked images indicate a significant change in depth in the control. However, the change in thickness for the Rhodamine in the bulk control is not nearly as much as the thickness changes noted in the AZO in the bulk system.

FIGS. 14-29 include images of biofilm disruption and removal from the surface of a glassy substrate with the disclosed light sensitive AZO-based polymer networks. The biofilm used for these images was a *Pseudomonas aeruginosa* (PA01) culture, although the AZO-based materials would also work for other biofilms.

The following test conditions were used for the images in FIGS. 14-24, unless indicated otherwise:

Light Exposure: Elipar Dental lamp 430-480 nm at 700 mW/cm$^2$.

Water Wash: Quick 5 second submersion and slight swirling of sample.

Base of sample was then dried and placed back on microscope for imaging after exposure to visible.

Temperature Rise: no greater than 1° C. during high intensity exposure.

Figure 14A:
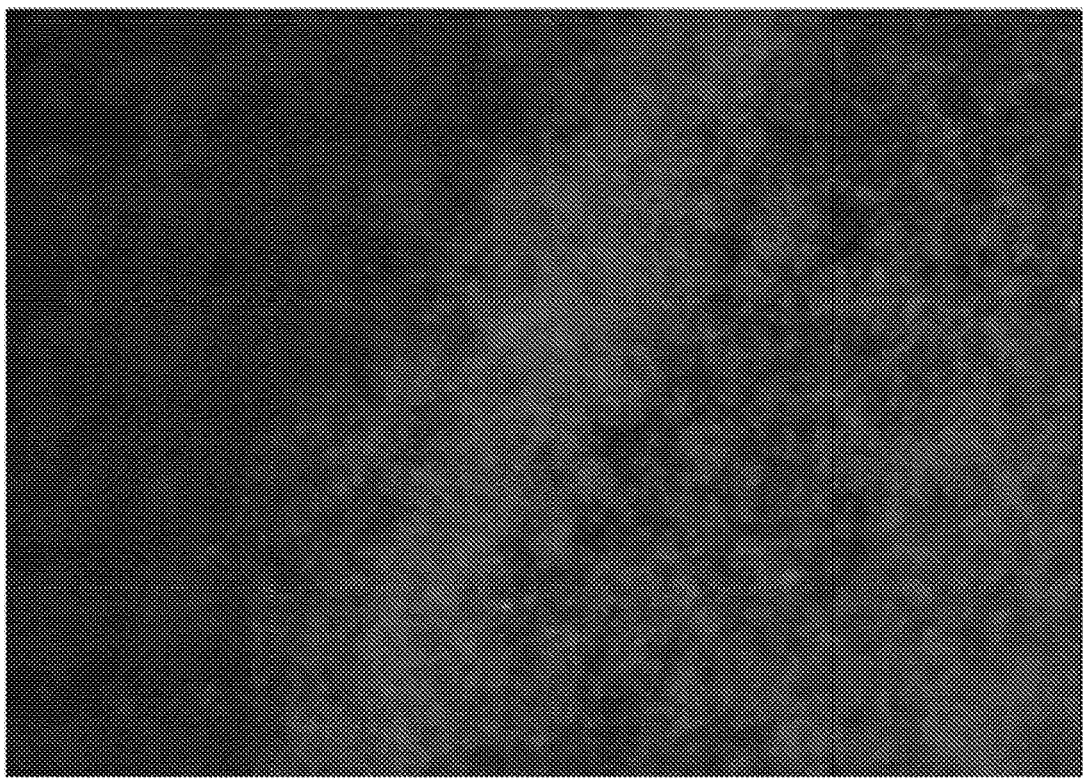
Figure 14B:
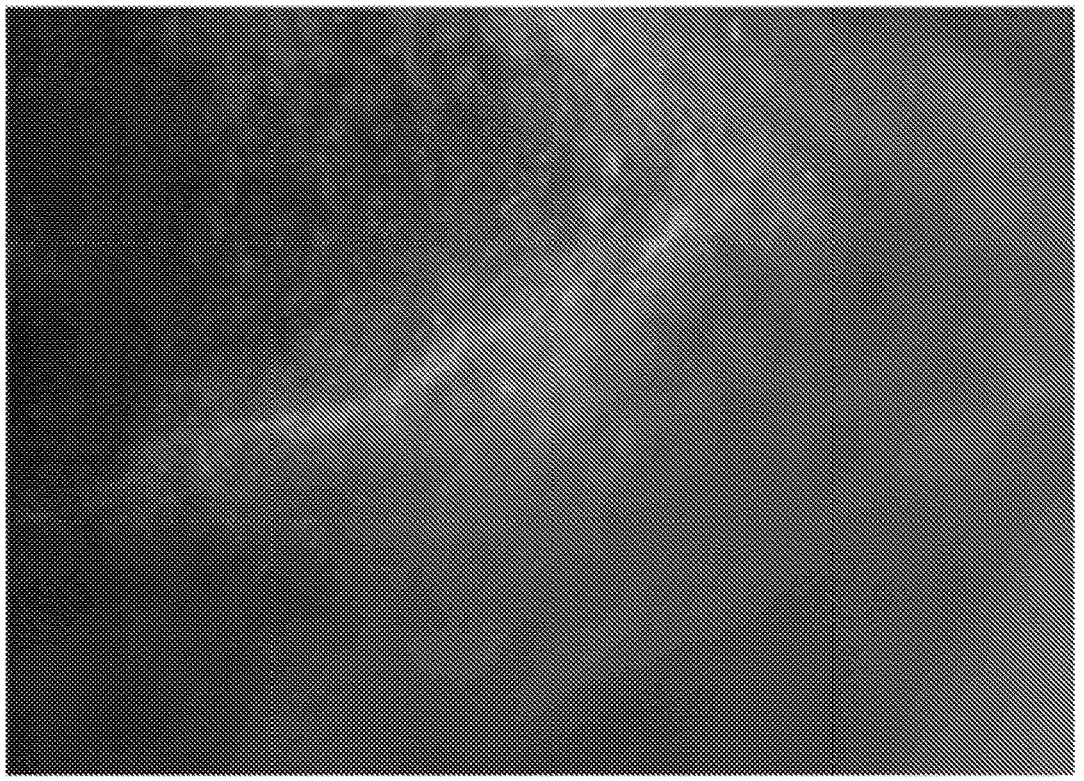

FIGS. 14A and 14B are photomicrograph images of an example base polymer before (FIG. 14A) and after (FIG. 14B) a 30 second light exposure and gentle water wash, the base polymer having an AZO coating, with no pattern. As seen in FIGS. 14A and 14B, there was substantial random growth of biofilm on the surface of the base polymer. There was no observed effect after light exposure and water wash.

Figure 15A:
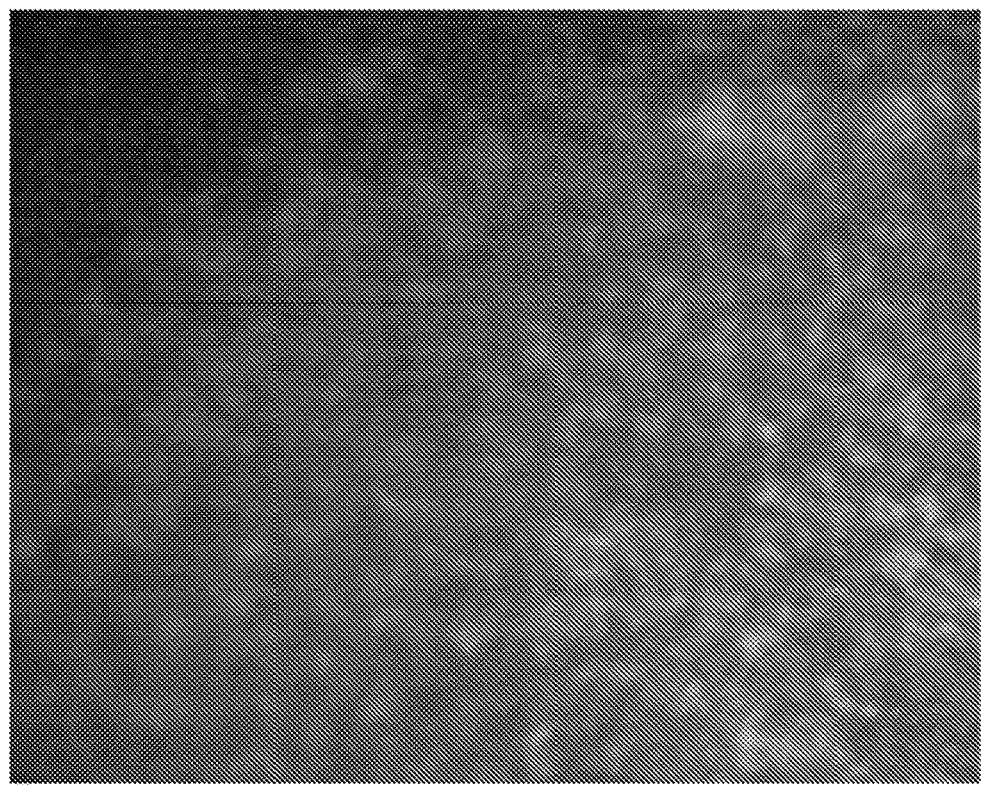
Figure 15B:
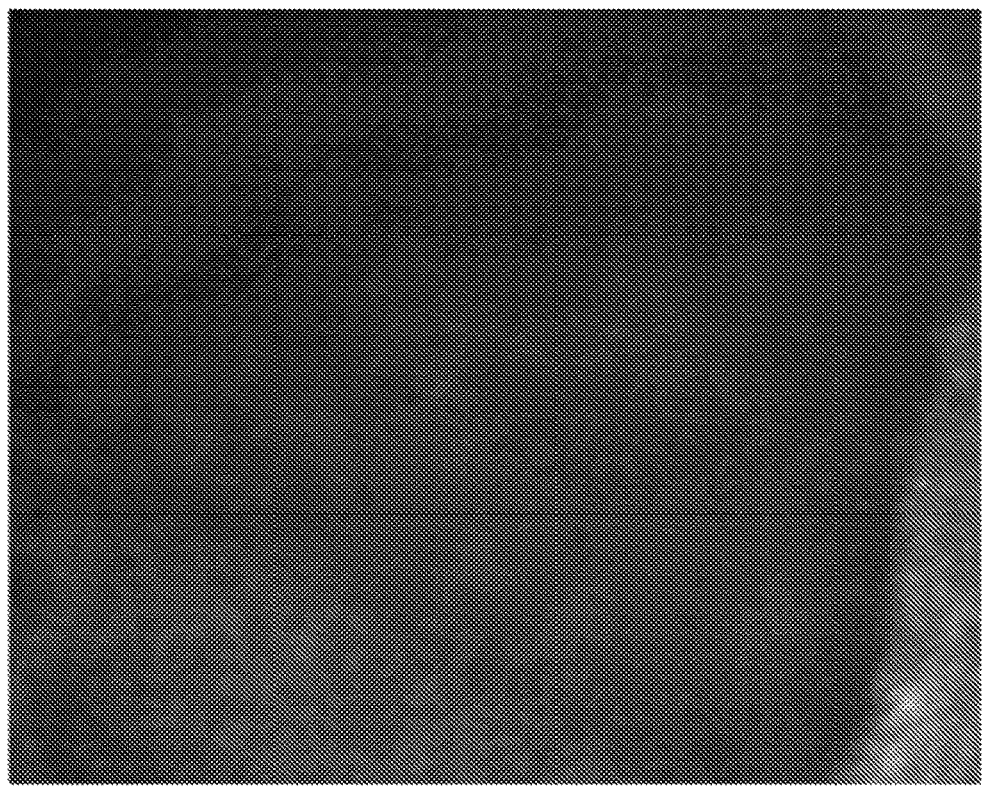

FIGS. 15A and 15B are photomicrograph images of an example base polymer before (FIG. 15A) and after (FIG. 15B) a 30 second light exposure and gentle water wash, with an AZO coating, with no pattern. As seen in FIGS. 15A and 15B, there was substantial random growth on the surface of the base polymer. After light exposure and gentle water wash, a disruption of the biofilm was observed and clumped "bands" of bacteria were visible on the surface while other areas had no remaining bacteria.

Figure 16A:
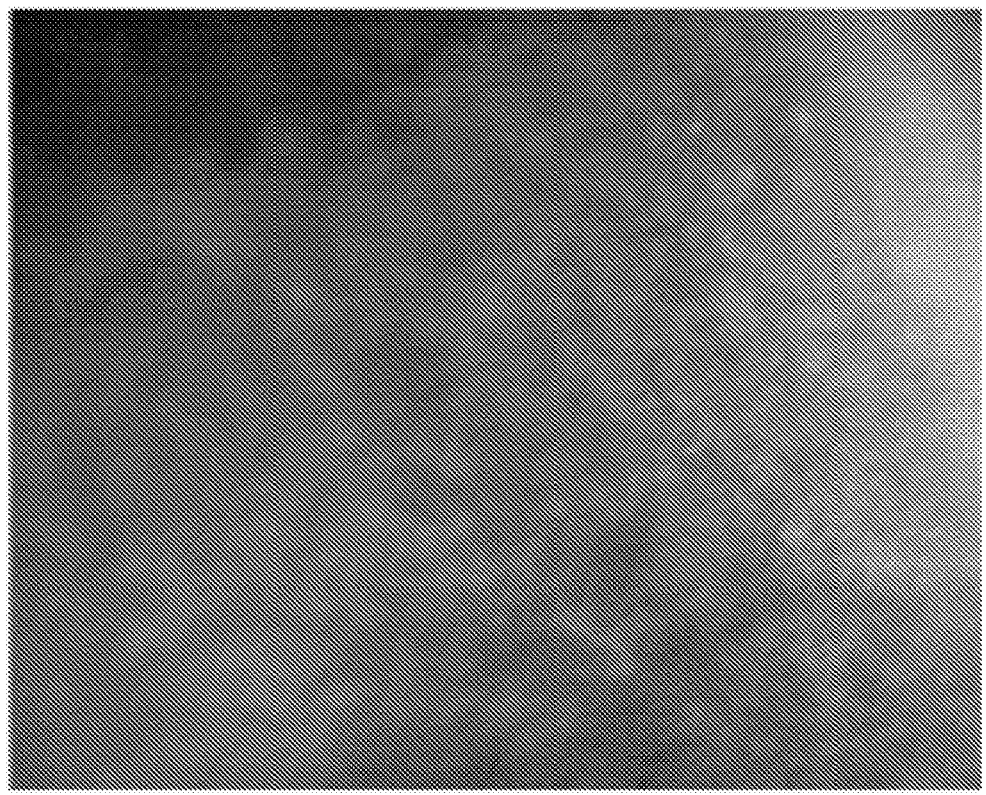
Figure 16B:
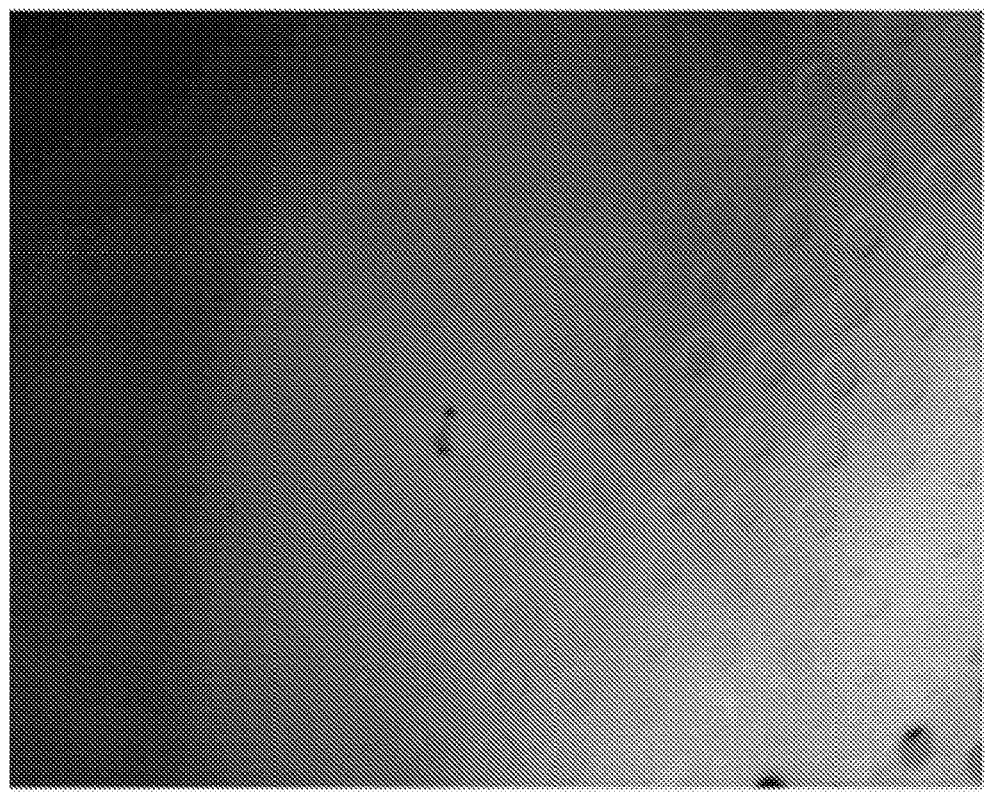

FIGS. 16A and 16B are photomicrograph images of an example base polymer before (FIG. 16A) and after (FIG. 16B) a 30 second light exposure and gentle water wash, with a patterned AZO coating. As seen in FIGS. 16A and 16B, there was substantial growth initially before exposure. After light exposure and water wash, a minimal amount of clumps of bacteria remained while others washed away and the underlying AZO surface pattern was exposed.

Figure 17A:
Figure 17B:
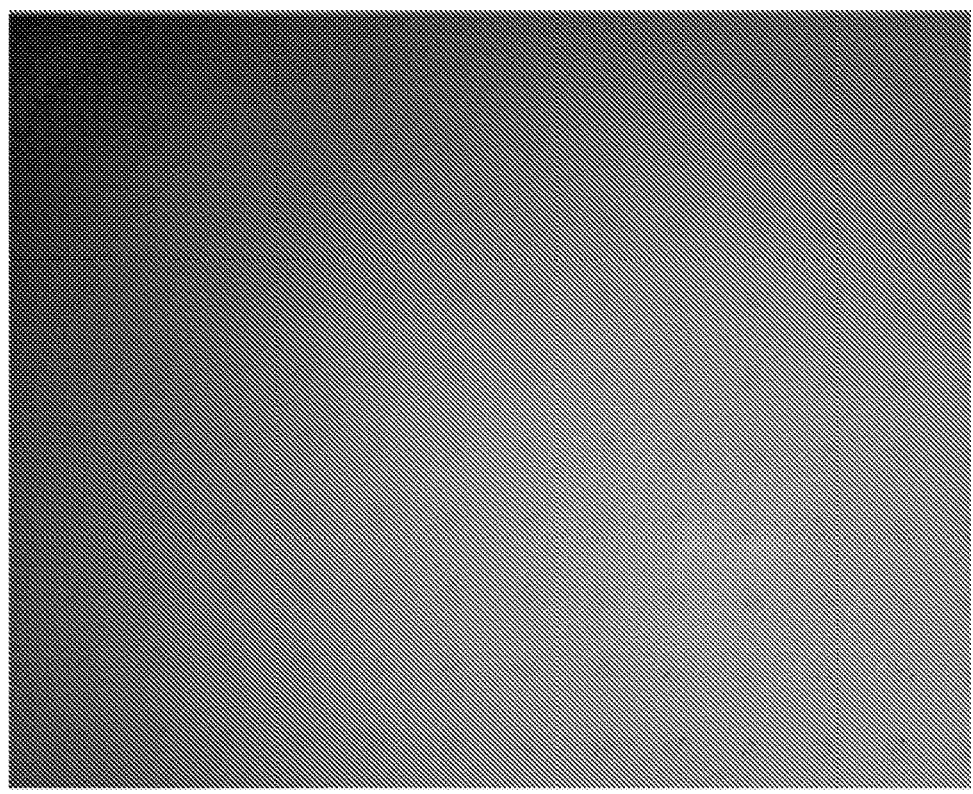

FIGS. 17A and 17B are photomicrograph images of an example base polymer before (FIG. 17A) and after (FIG. 17B) a 30 second light exposure and gentle wash, with a patterned AZO coating. As shown in FIG. 17A, there was substantial growth initially before exposure.

After light exposure and water wash, as shown in FIG. 17B, there was minimal amount of clumps of bacteria while others washed away and the underlying AZO surface pattern was exposed.

Figure 18A:
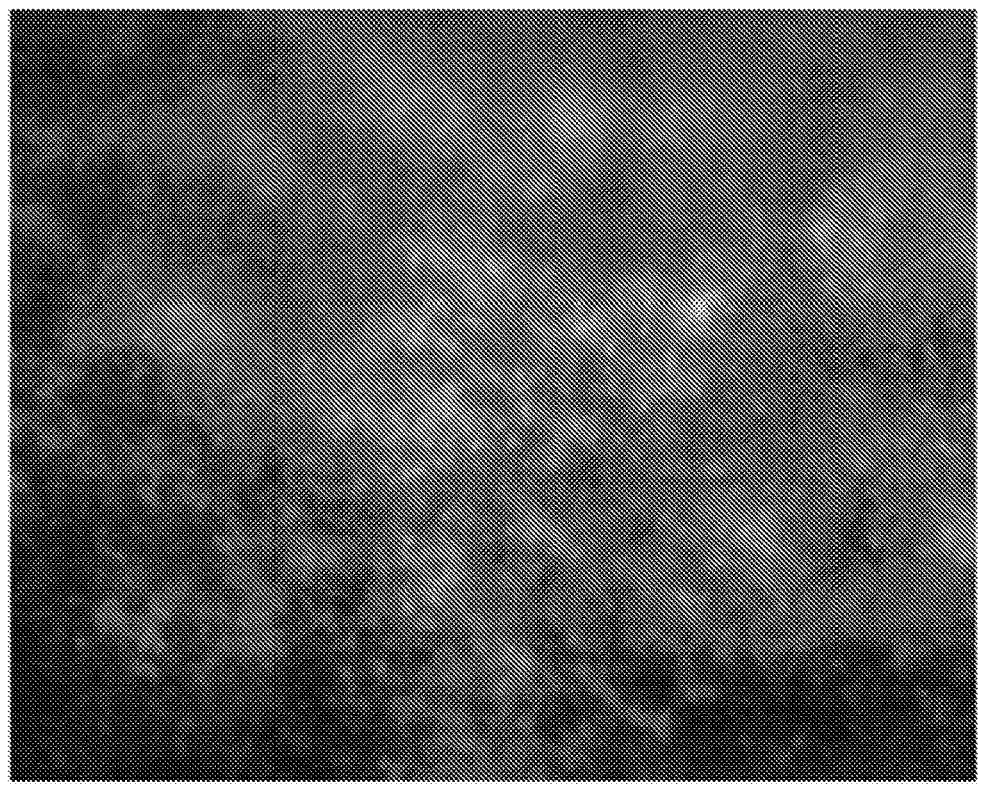
Figure 18B:
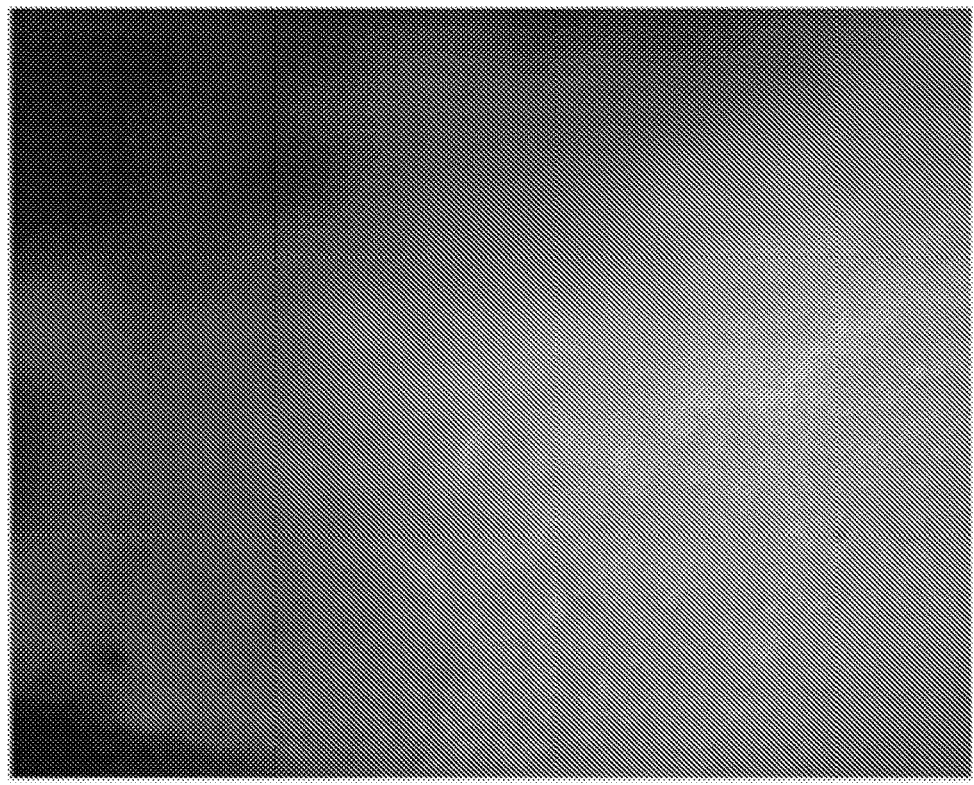

FIGS. 18A and 18B are photomicrograph images of an example base polymer (FIG. 18A) and the same example base polymer after a gentle wash, patterned AZO coating, but with no light exposure (FIG. 18B). Some removal of the AZO coating occurred during the wash step but not nearly as much as the samples that were irradiated with light (e.g., FIG. 17B).

Figure 19A:
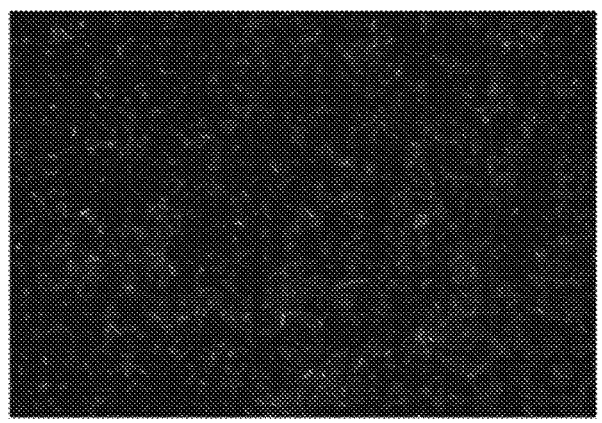
Figure 19B:
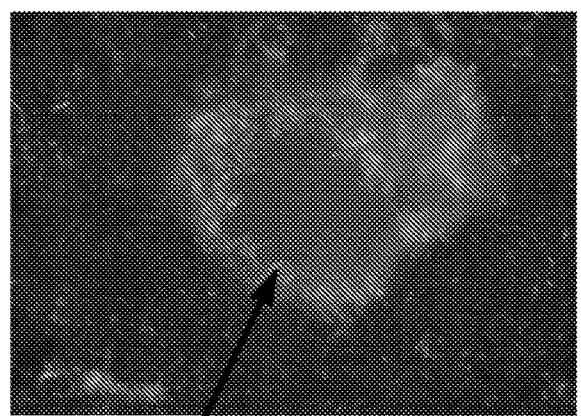
Figure 19C:
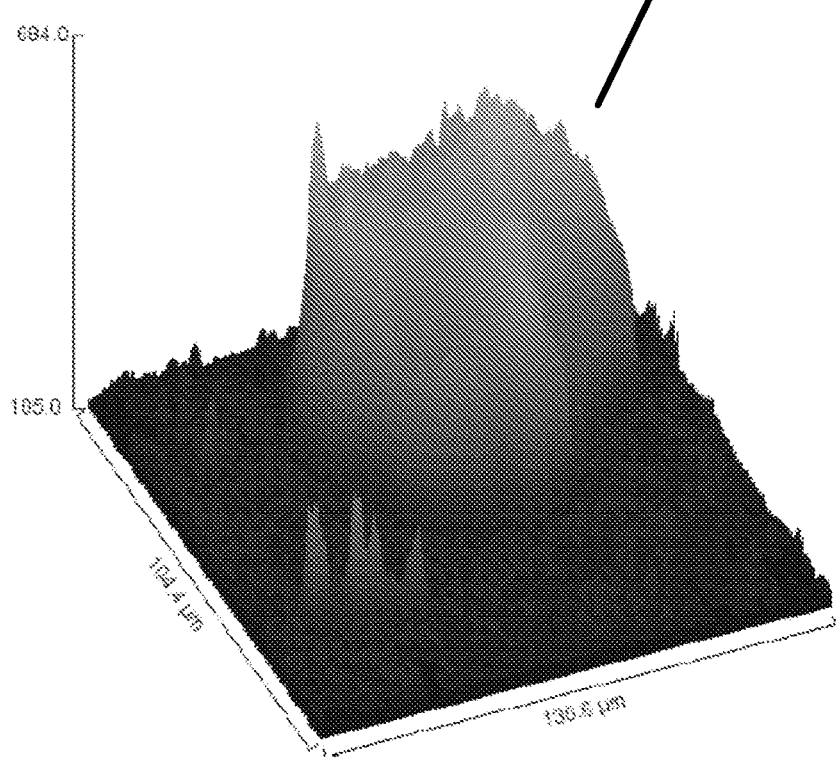
Figure 20A:
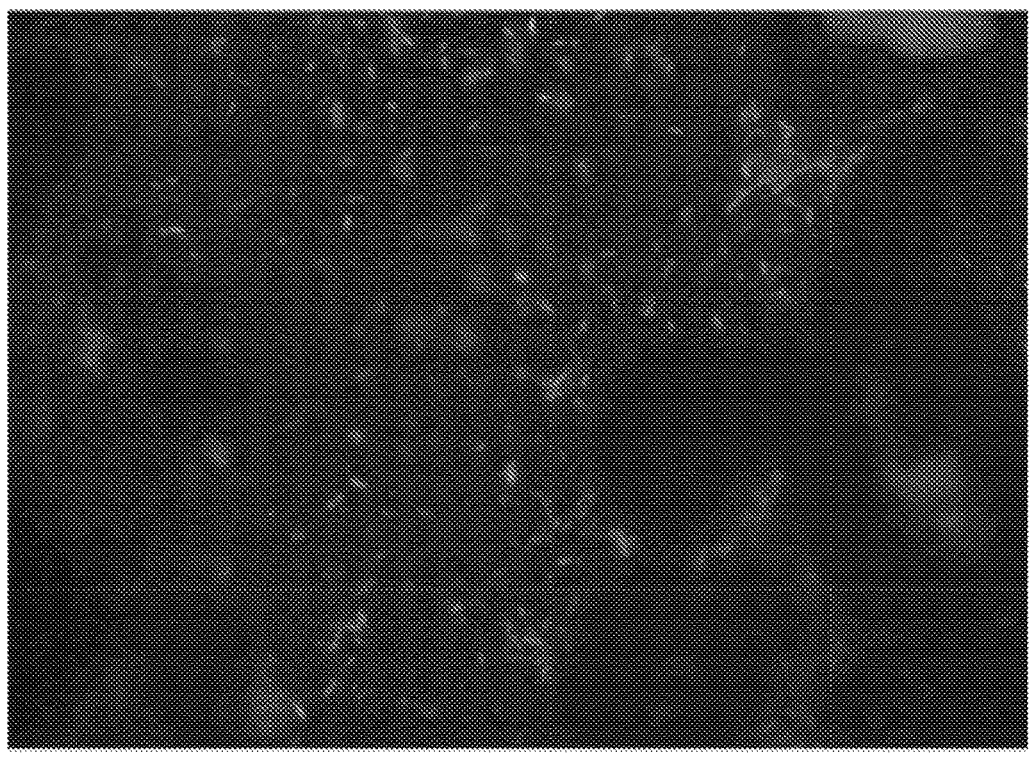
Figure 20B:
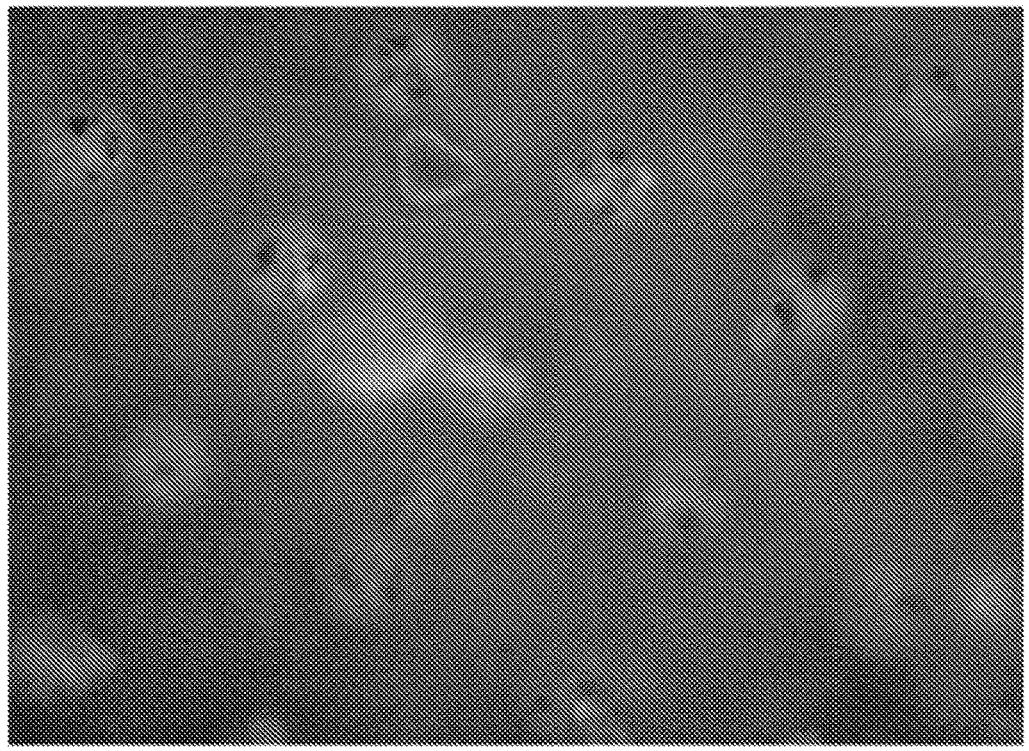
Figure 21A:
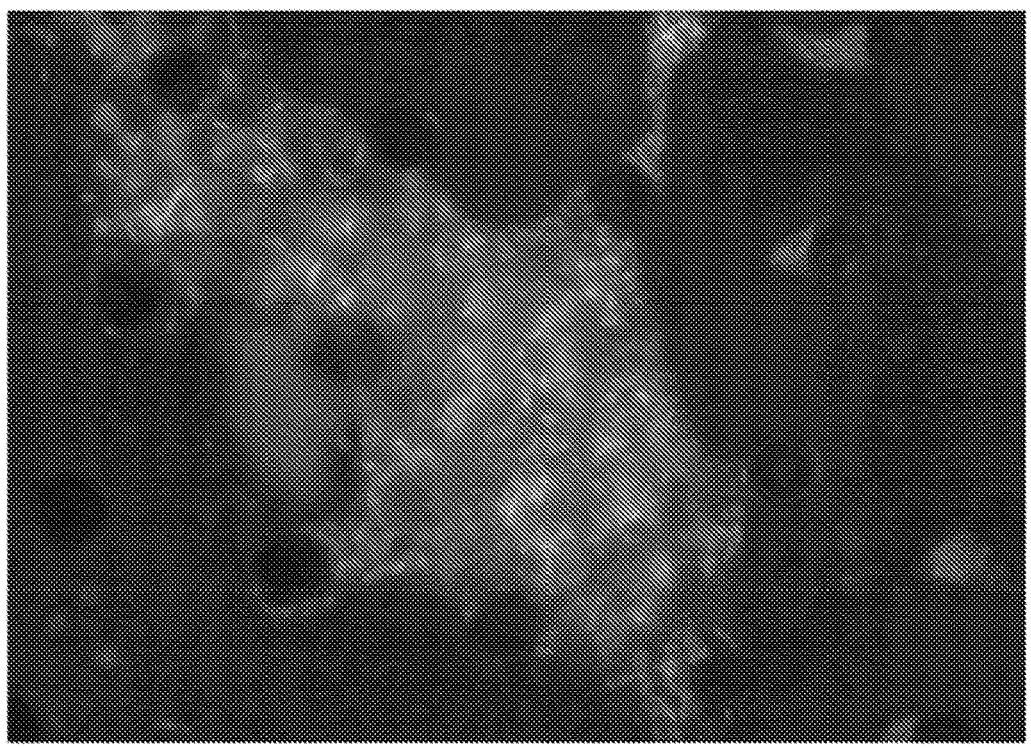
Figure 21B:
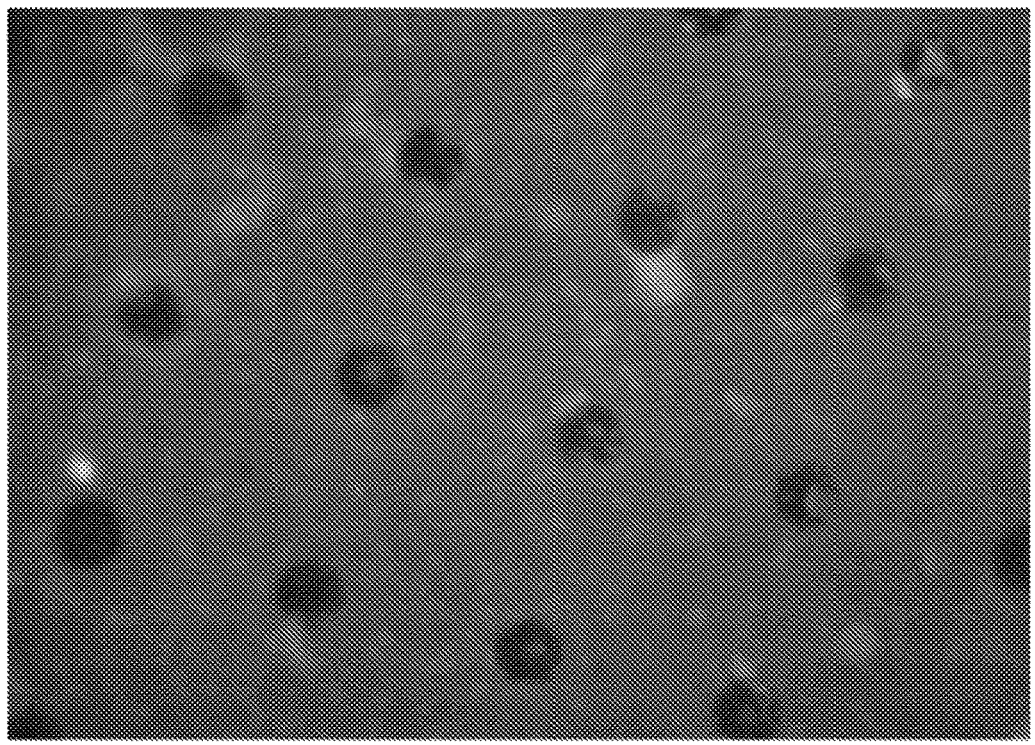

FIGS. 19A and 19B are photomicrograph images of an example base polymer before (FIG. 19A) and after (FIG. 19B) light exposure and gentle wash, FIG. 19C is a graphical representation of a surface profile at the AZO/biofilm interface, Base Polymer (No AZO) 63× oil.

FIGS. 20A and 20B, and FIGS. 21A and 21B are photomicrograph images of an example base polymer before (FIG. 20A, FIG. 21A) and after (FIG. 20B, FIG. 21B) light exposure and gentle wash, AZO patterned Base Polymer 63× oil. The images show substantial removal of biofilm.

FIGS. 22A, 22B, 22C, 22D are photomicrograph images of an example base polymer before (FIG. 22A, FIG. 22C) and after (FIG. 22B, FIG. 22D) light exposure and gentle wash. FIGS. 22A, 22B, 22C, 22D show a patterned AZO time lapse 63× oil. The images show water wash is desired for removal.

Figure 23A:
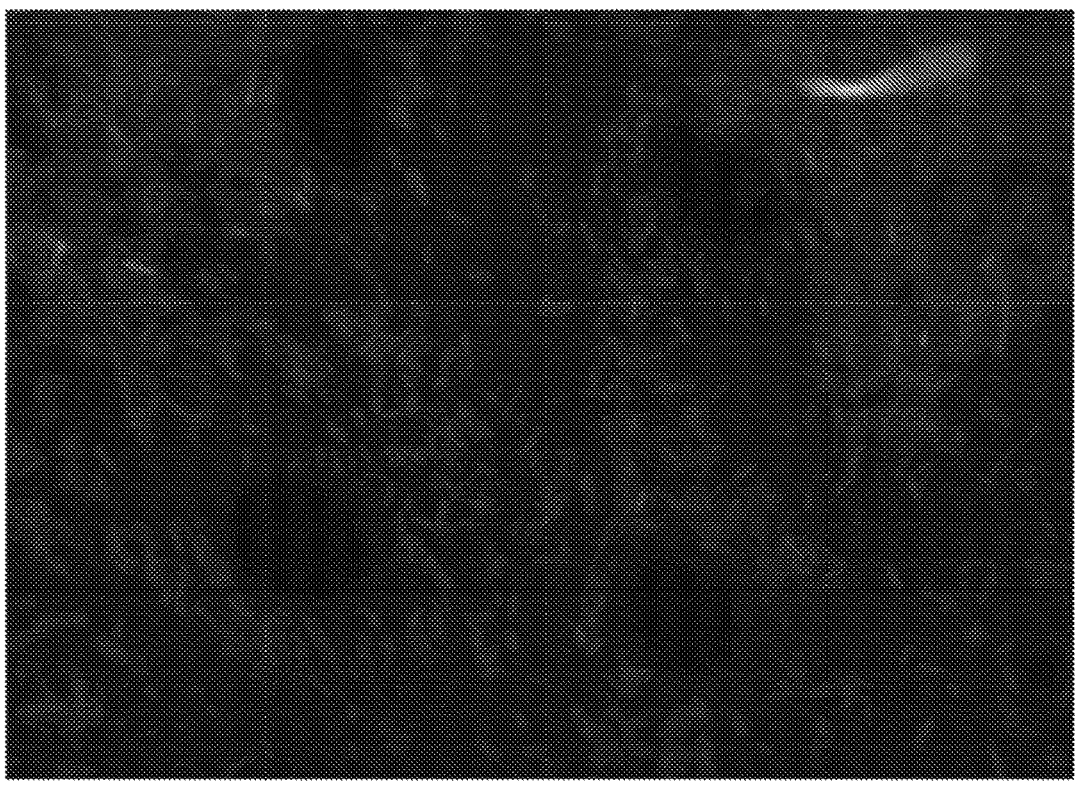
Figure 23B:
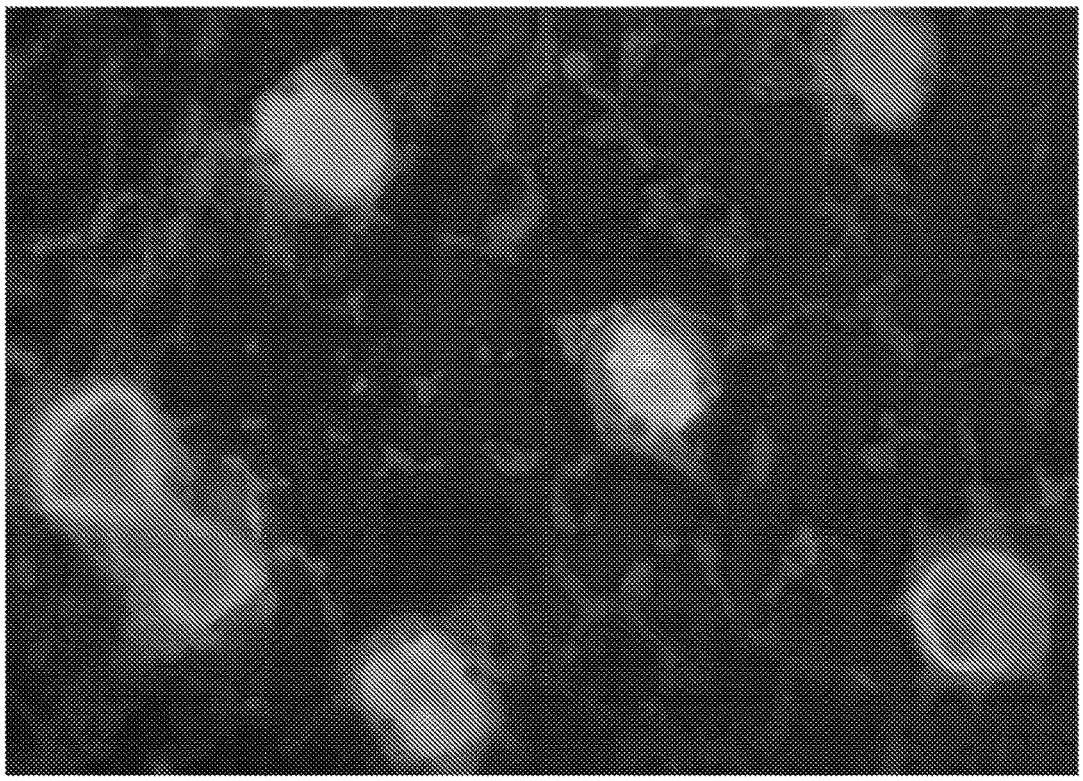

FIGS. 23A and 23B are photomicrograph images of an example base polymer before (FIG. 23A) and after (FIG. 23B) 30 second light exposure and gentle water wash. FIGS. 23A and 23B show images of AZO patterned base polymer 100× oil. An effect is observed, manifesting as a change in height, both in the presence and absence of AZO. The observed effect, however, is 9 times greater in the presence of AZO. Rhodamine's presence in the system may be causing an artifact in the imaging place under confocal microscopy.

FIGS. 24-29 are confocal images of substrates with AZO and biofilm. The temperature rise was monitored to ensure that the biofilm was removed as a result of AZO-activation and not temperature. The following test conditions were used for the images in FIGS. 24-29:

Light Exposure: Irradiate the sample with an Elipar Dental lamp 430-480 nm at 700 mW/cm$^2$.

Water Wash: Wash for 10 seconds, submersion and slight swirling of sample in milliQ water.

Base of sample dried with Kimwipe and placed back on microscope for imaging after exposure to visible light.

Temperature Rise: No greater than 1° C. during high intensity exposure.

Figure 24:
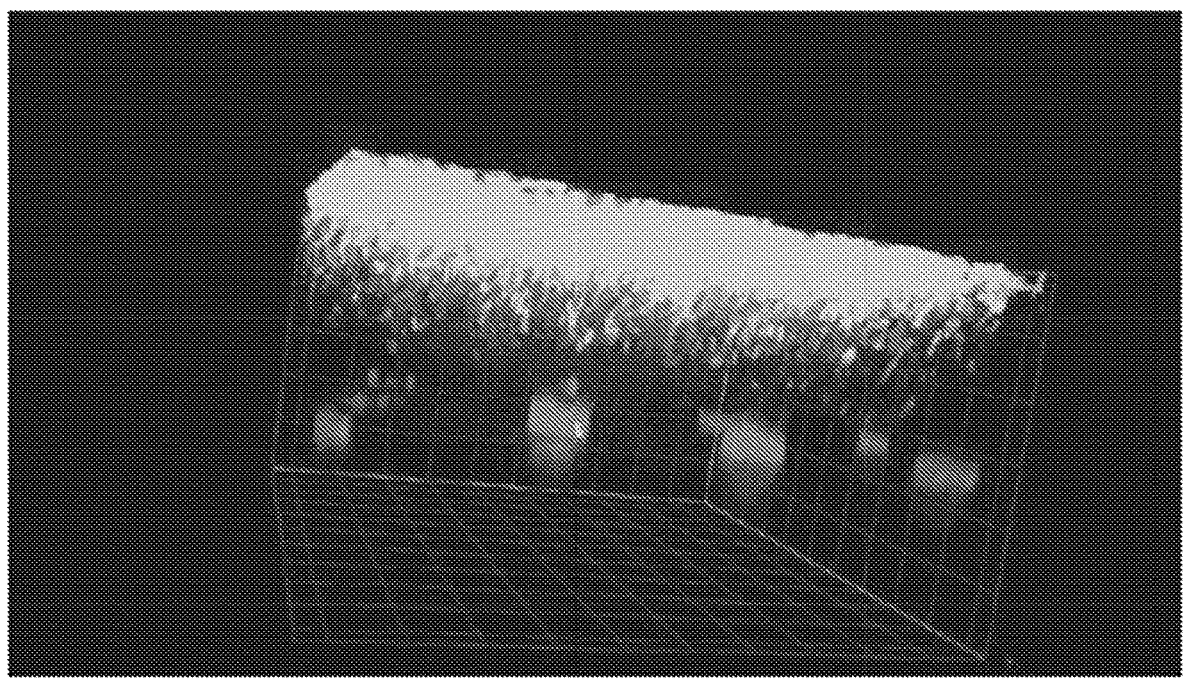

FIG. 24 is an example image of biofilm removal. The image shown in FIG. 24 is a first sample before exposure.

Figure 25:
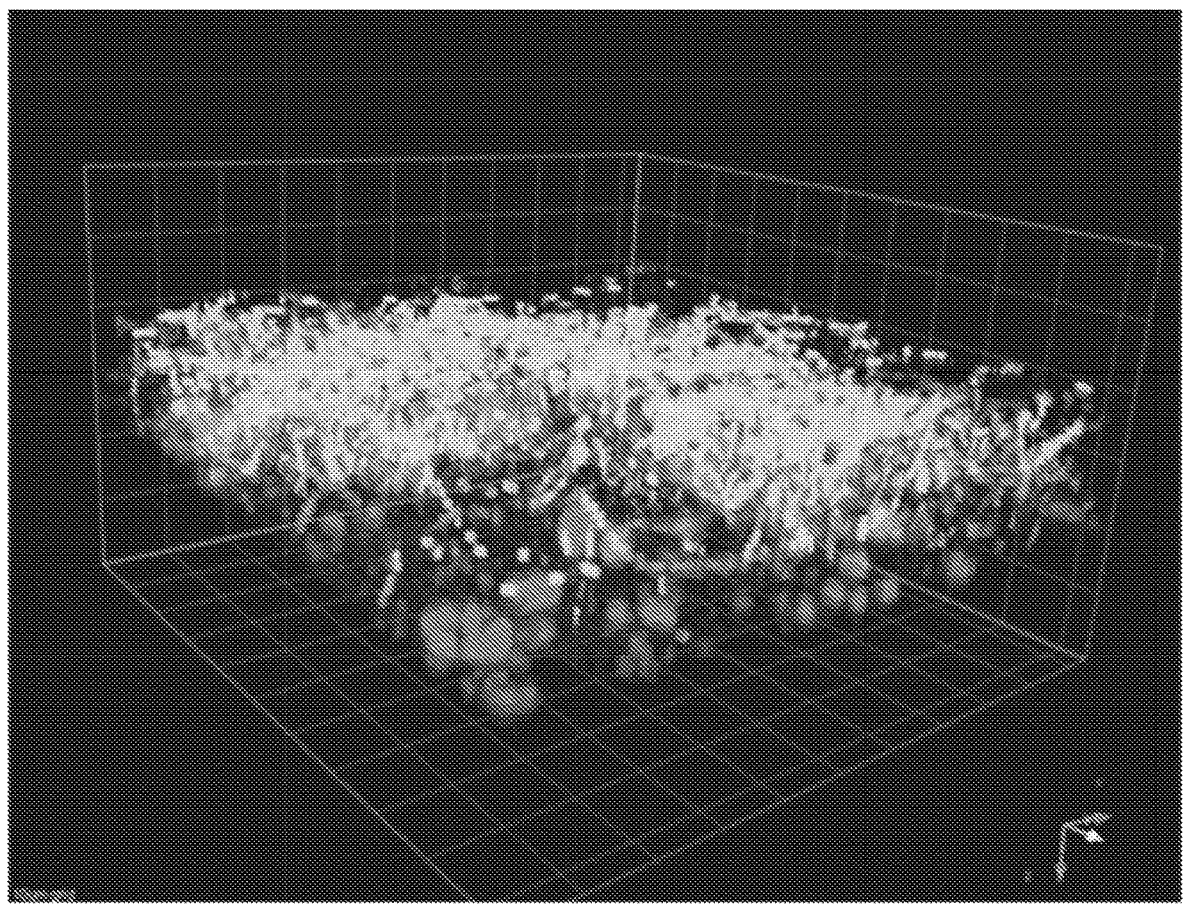

FIG. 25 is an example image of biofilm removal. The image shown in FIG. 25 is an initial image of a second sample with 63× oil.

Figure 26:
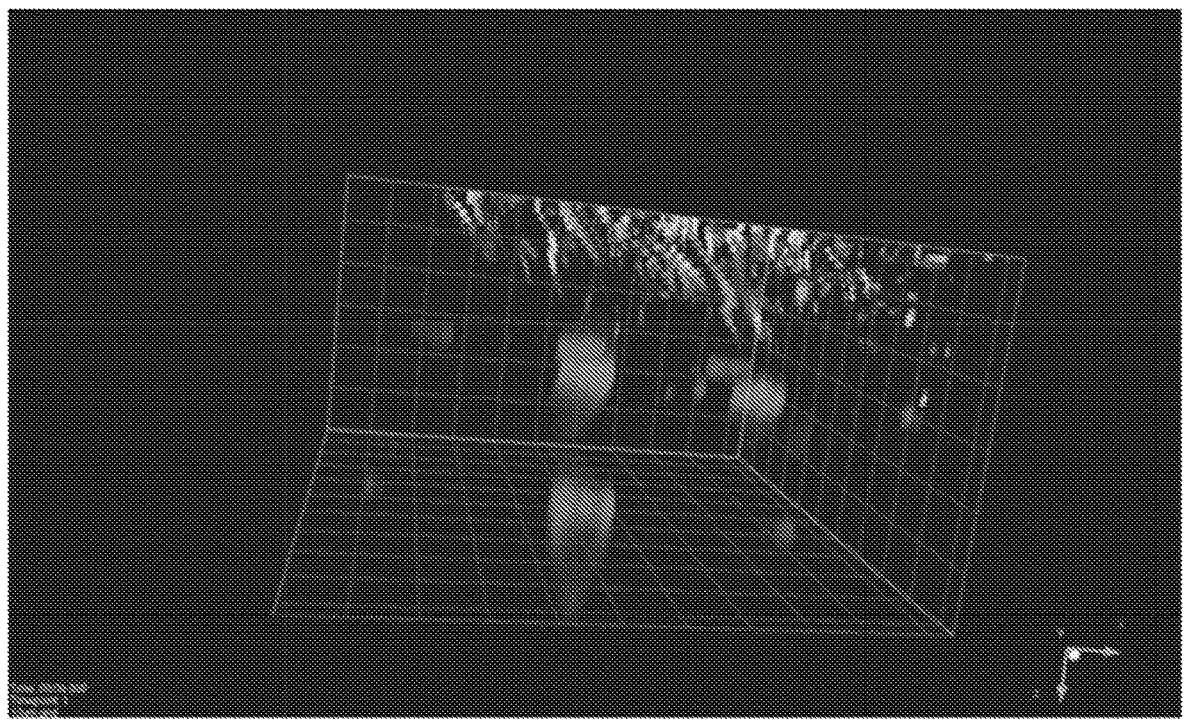

FIG. 26 is an example image of biofilm removal. The image shown in FIG. 26 is an image of the first sample (FIG. 24) after first exposure, water wash, and drying.

Figure 27:
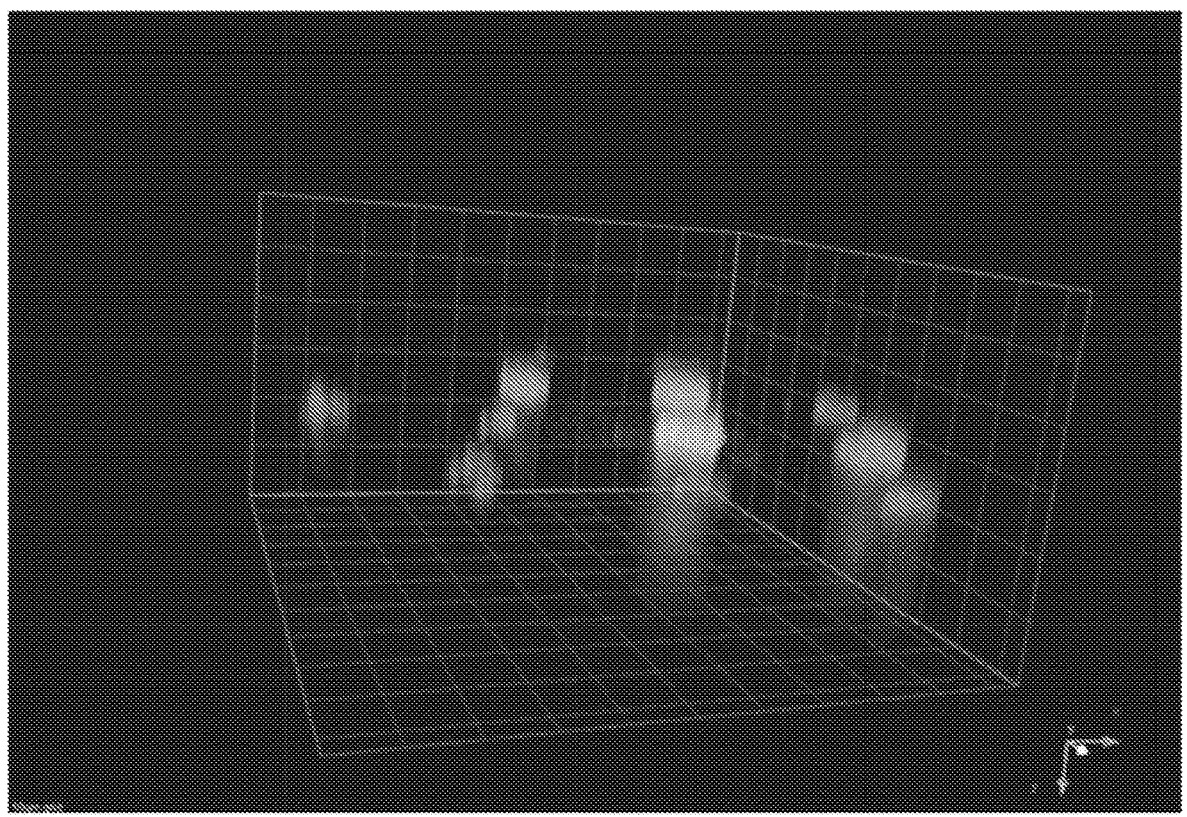

FIG. 27 is an example image of biofilm removal. The image shown in FIG. 27 is an image of the first sample (FIG. 24) after second exposure, water wash, and drying.

Figure 28:
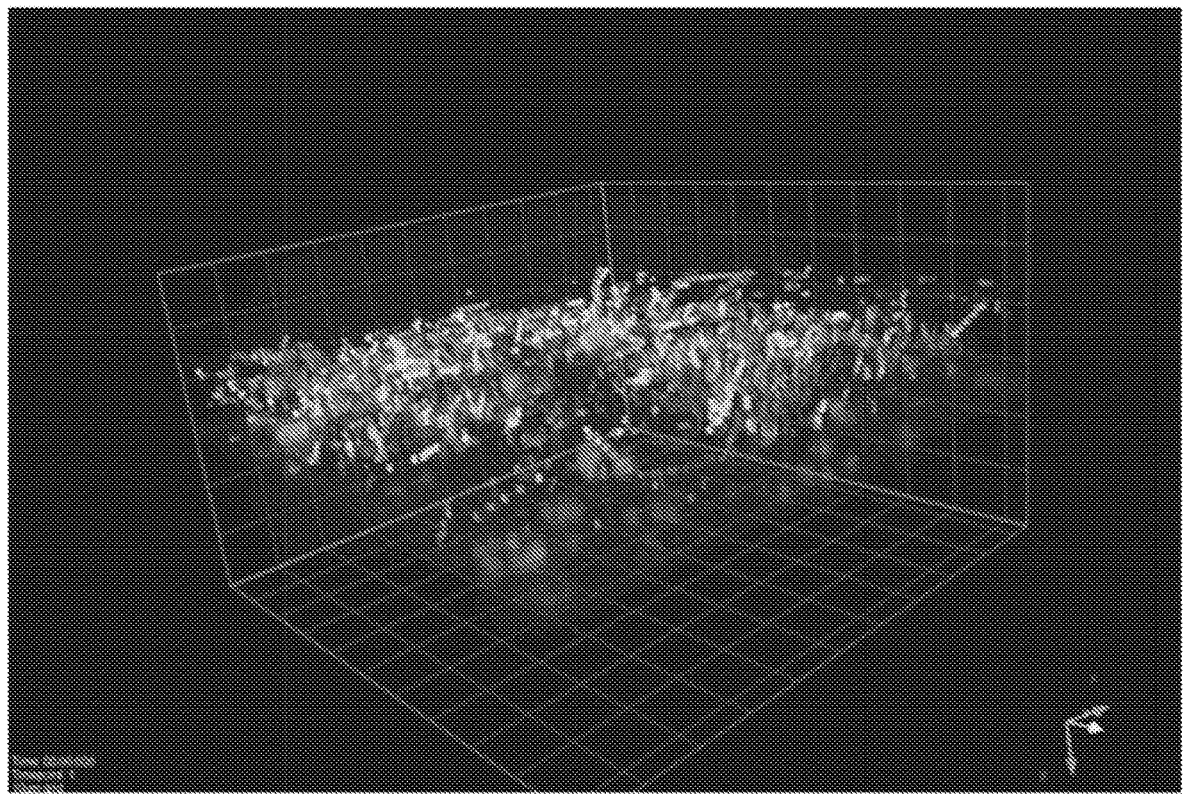

FIG. 28 is an example image of biofilm removal. The image shown in FIG. 28 is a third sample before exposure.

Figure 29:
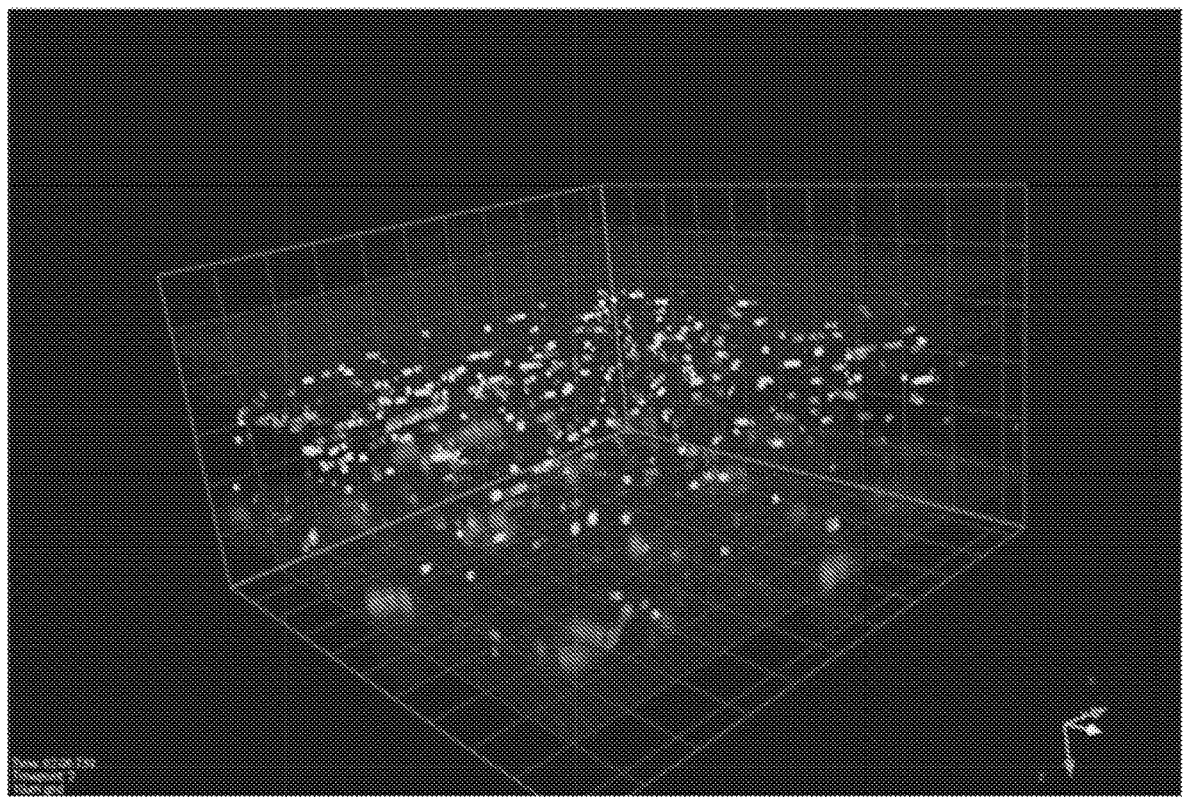

FIG. 29 is an example image of biofilm removal. The image shown in FIG. 29 is the third sample (FIG. 28) during light exposure.

The AZO-based polymer networks can additionally be used to remove biofilm such as *Pseudomonas aeruginosa* (PA01) from substrates, particularly, from contact lenses.

Figure 30:
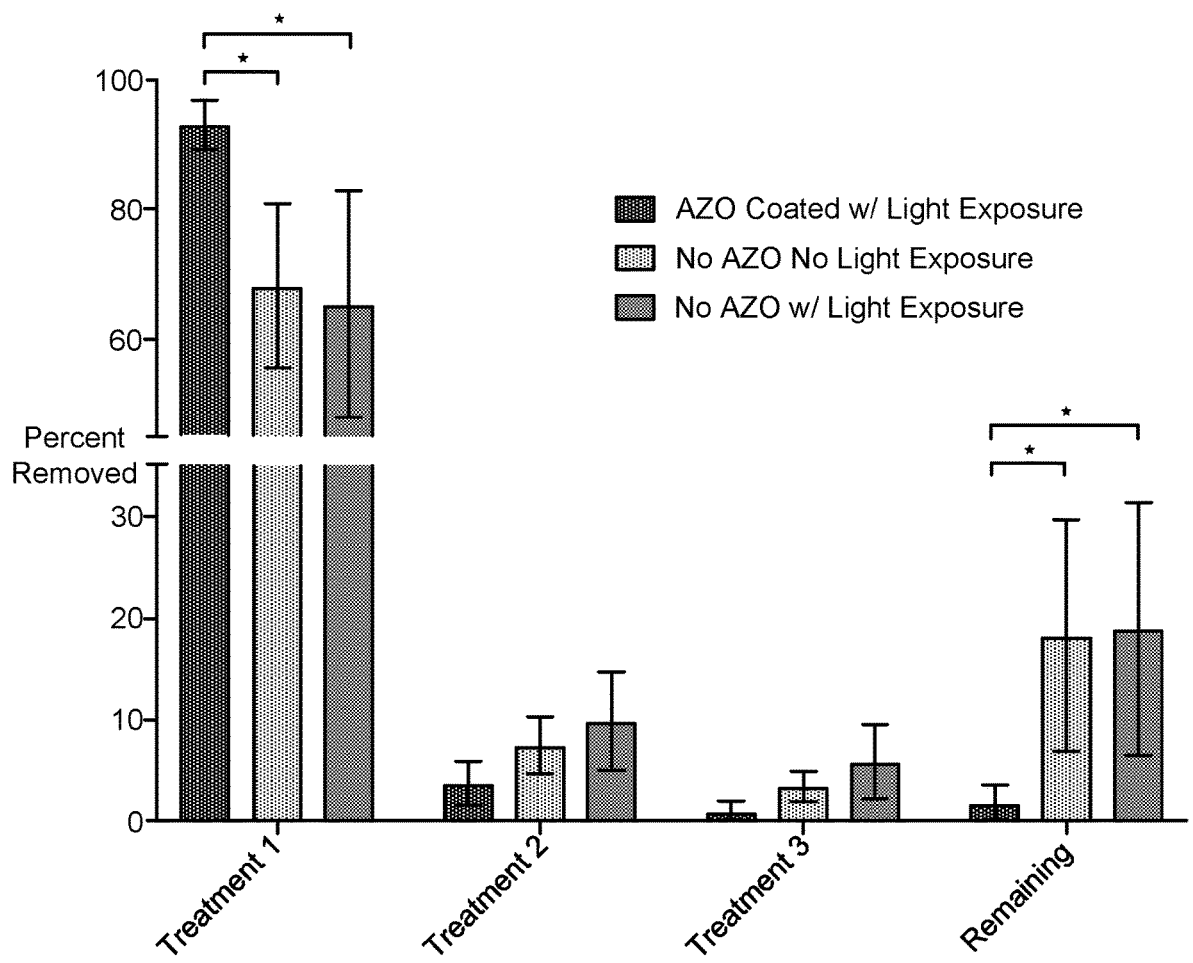
FIG. 30 is a graphical representation comparing *Pseudomonas aeruginosa* biofilm removal from an example base substrate.

*Pseudomonas aeruginosa* (PA01) cultures were grown for 20 hours in 1/10×LB inoculated onto a AZO-based polymer network coating on a PMMA/TEGDMA glassy substrate to form biofilms. FIG. 30 shows the percent of PA01 removed after light exposure of the AZO-coated substrate, after light exposure of a similar glassy substrate without an AZO-based coating, and after no light exposure of a similar glassy substrate without an AZO-based coating. The amount of PA01 remaining after three subsequent treatments is significantly less for the AZO-coated substrate that had been exposed to light.

Figure 31:
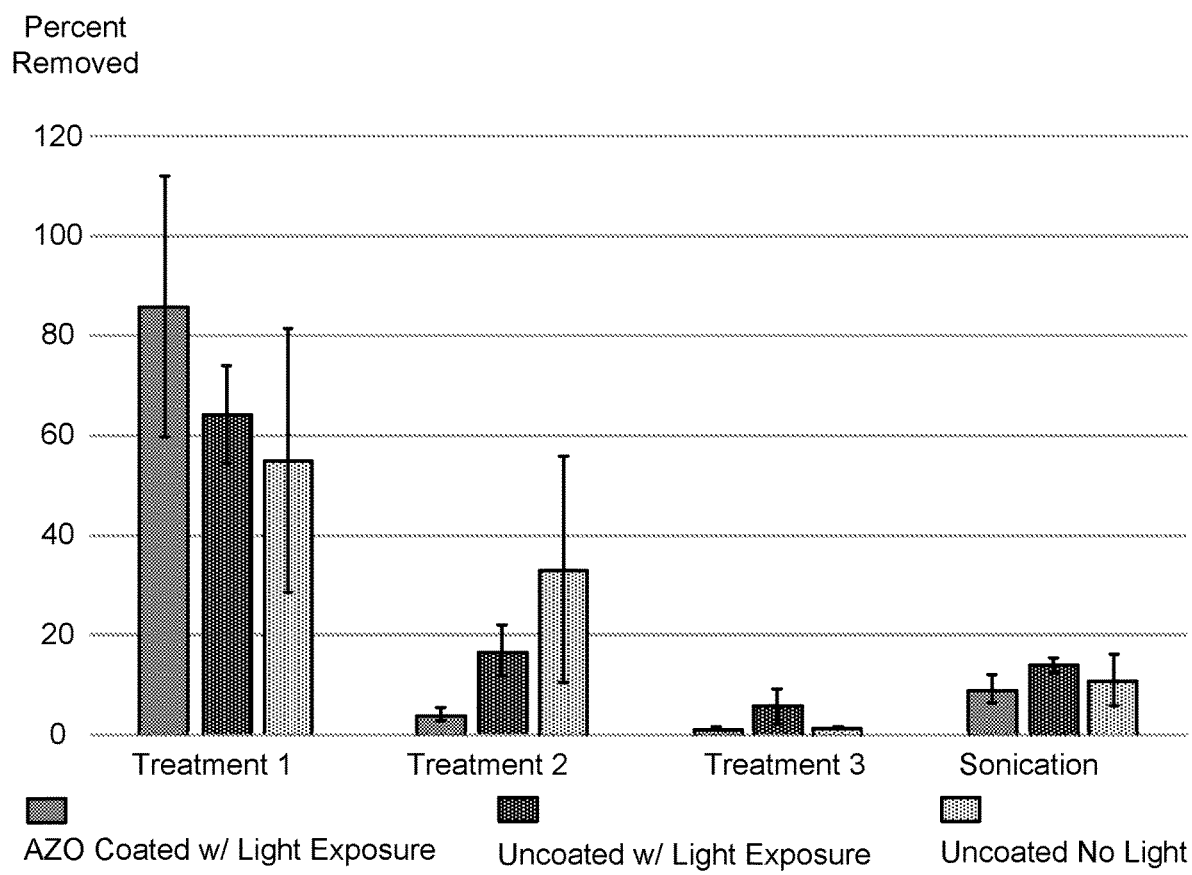
FIG. 31 is a graphical representation comparing MRSA biofilm removal from an example base substrate.

FIG. 31 shows similar results for methicillin-resistant *Staphylococcus aureus* (MRSA); FIG. 31 shows the percent of MRSA removed after light exposure of the AZO-coated substrate, after light exposure of a similar glassy substrate without an AZO-based coating, and after no light exposure of a similar glassy substrate without an AZO-based coating. The results for three subsequent treatments are shown compared to a conventional sonication treatment.

Figure 32:
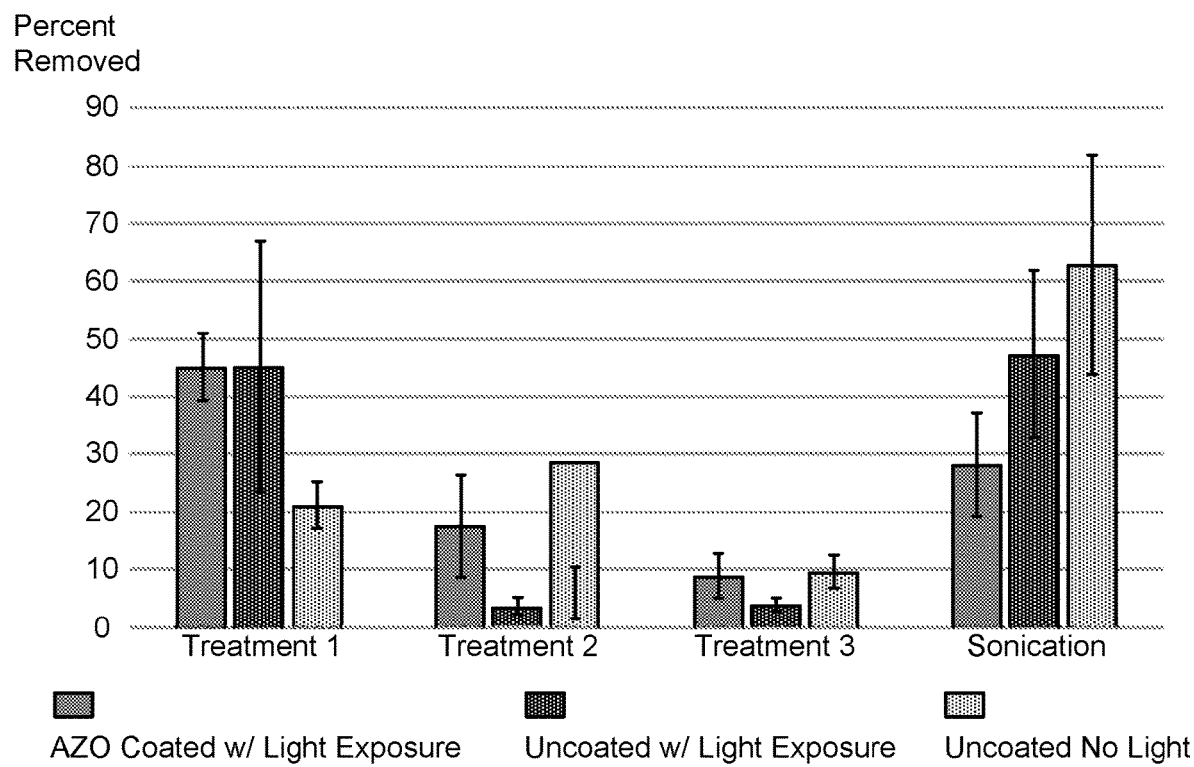
FIG. 32 is a graphical representation comparing UPEC biofilm removal from an example base substrate.

FIG. 32 shows similar results for UroPathogenic *Escherichia coli* (UPEC); FIG. 32 shows the percent of UPEC removed after light exposure of the AZO-coated substrate, after light exposure of a similar glassy substrate without an AZO-based coating, and after no light exposure of a similar glassy substrate without an AZO-based coating. The results for three subsequent treatments are shown compared to a conventional sonication treatment.

Figure 33:
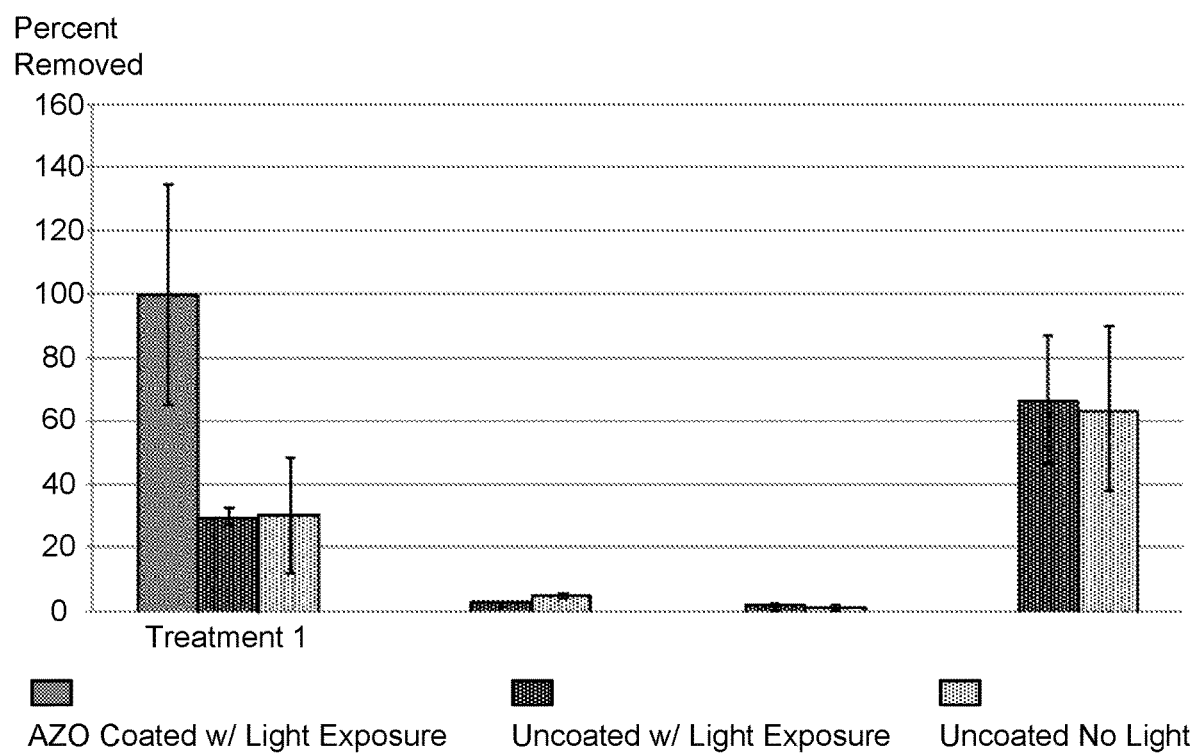
FIG. 33 is a graphical representation comparing *S. mutans* biofilm removal from an example base substrate.

FIG. 33 shows similar results for *Streptococcus mutans* (*S. mutans*); FIG. 33 shows the percent of *S. mutans* removed after light exposure of the AZO-coated substrate, after light exposure of a similar glassy substrate without an AZO-based coating, and after no light exposure of a similar glassy substrate without an AZO-based coating. The results for three subsequent treatments are shown compared to a conventional sonication treatment.

The AZO-based polymer networks can also be used to inhibit the formation of biofilm such as *Pseudomonas aeruginosa* (PA01) on substrates, particularly, on lenses. Additionally, the AZO-based polymer networks can inhibit the growth of cells on the lenses.

Two different AZO-based polymer networks were made by using two different concentrations of AZO (50 mg/mL AZO; 0.5 mg/mL AZO). The coating formulation was 25 mg AZO, 500 microL DMF, and 0.02 g photoinitiator (TPO-L genocure) and the lens substrate was formed from HEA, Ebecryl 270, and photoinitiator (TPO-L genocure).

The coated lenses were exposed to ambient light (broad spectrum, multiple-wavelengths) on the bench-top and both the "residual cells" and the "attached cells" were observed. The presence of "residual cells" around the control (uncoated lens) as well as the AZO-coated material indicates that the materials are not cytotoxic. The number of "attached cells" on the surface of the AZO-coated lens is inversely proportional to the concentration of AZO present in the coating, implying that the AZO impacts the ability of the cells to attach to the surface of the lens.

Figure 34:
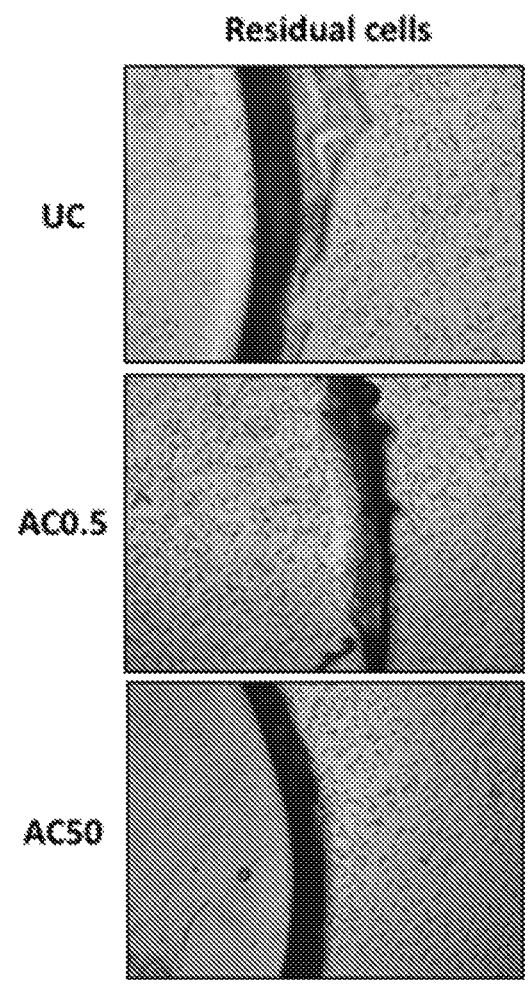
FIG. 34 are photomicrograph images of residual cells on three lens substrates.
Figure 35:
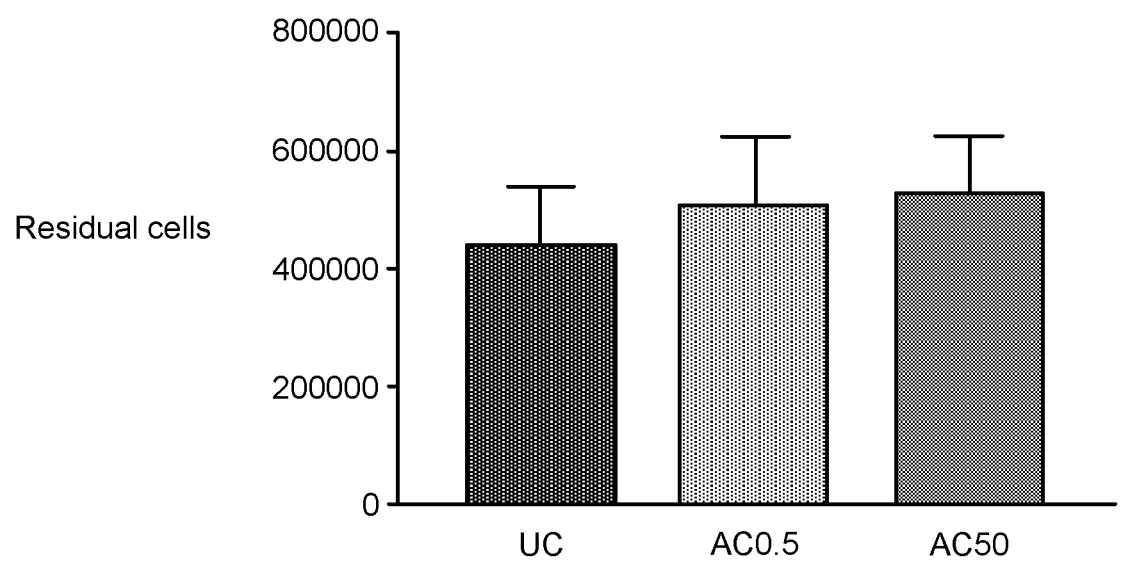
FIG. 35 is a graphical representation comparing residual cells on three lens substrates.

FIG. 34 shows photomicrographs of the residual cells on the uncoated (control) lens, the lens having the AZO 0.5 concentration, and the lens having the AZO 50 concentration. FIG. 35 shows numerically the number of residual cells on the uncoated (control) lens, the lens having the AZO 0.5 concentration, and the lens having the AZO 50 concentration.

Figure 36:
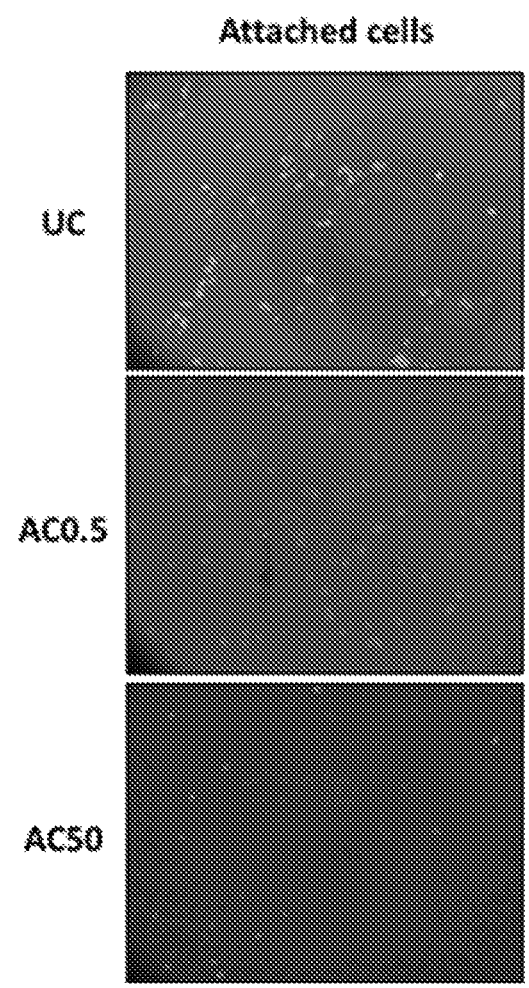
FIG. 36 are photomicrograph images of attached cells on three lens substrates.
Figure 37:
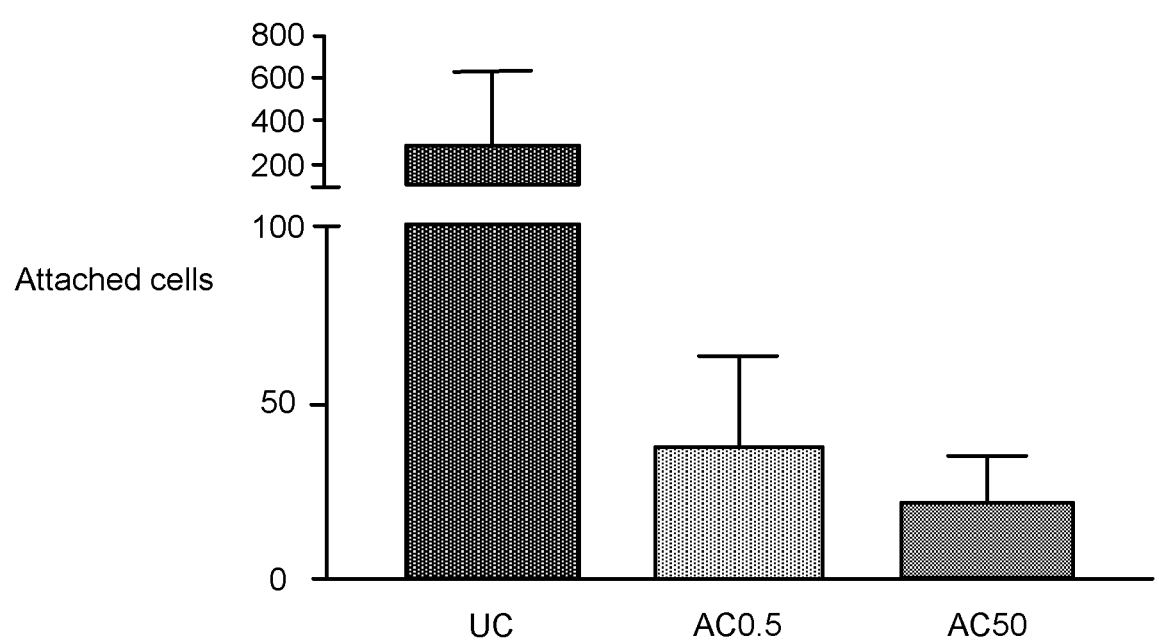
FIG. 37 is a graphical representation comparing attached cells on three lens substrates.

FIG. 36 shows photomicrographs of the attached cells on the uncoated (control) lens, the lens having the AZO 0.5 concentration, and the lens having the AZO 50 concentration. FIG. 37 shows numerically the number of attached cells on the uncoated (control) lens, the lens having the AZO 0.5 concentration, and the lens having the AZO 50 concentration.

The above specification, examples, and data provide a complete description of the structure, features and use of exemplary implementations of the invention. Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A method comprising:
   polymerizing an azobenzene (AZO)-based polymer network from a composition comprising AZO and forming an AZO-based system comprising the AZO-based polymer network and a base substrate; and
   irradiating the AZO-based system to initiate mechanical oscillation due to trans-cis-trans isomerization and/or photofluidization of the AZO-based polymer network to disrupt any film present on a surface of the base substrate and/or inhibit formation of any film on the surface of the base substrate.

2. The method of claim 1, wherein the base substrate comprises at least one of methyl methacrylate (MMA), poly(methyl methacrylate) (PMMA), and triethylene glycol dimethacrylate (TEGDMA).

3. The method of claim 1, further comprising:
   covalently tethering the AZO-based polymer network to the base substrate with a thermal initiator and acrylated AZO.

4. The method of claim 1, wherein forming the AZO-based system comprises polymerizing the AZO-based polymer network to form a glassy AZO-based system.

5. The method of claim 4, wherein forming the AZO-based system comprises:
   drop casting the AZO-based polymer network as a surface coating on the base substrate; and
   thermally curing the surface coating.

6. The method of claim 1, wherein the AZO-based polymer network is polymerized via UV or thermal free-radical initiated polymerization.

7. The method of claim 1, wherein the base substrate is a part of a surgical instrument, a dental device, or a wound dressing.

8. The method of claim 1, wherein the base substrate is a part of industrial equipment for food, fermentation equipment, or equipment for a water treatment system.

9. The method of claim 1, wherein the base substrate is part of an ocular lens.

10. The method of claim 1, wherein the base substrate is a dental surface being a tooth, a sealed tooth, a denture, a composite, or a sealed composite.

11. The method of claim 1, wherein the film being disrupted and/or inhibited from formation is a biofilm.

12. The method of claim 1, wherein the film being disrupted and/or inhibited from formation comprises cells.

* * * * *